(12) United States Patent
Hurov et al.

(10) Patent No.: US 10,101,331 B2
(45) Date of Patent: *Oct. 16, 2018

(54) METHODS OF EVALUATING PATIENTS USING E-CADHERIN OR VIMENTIN

(71) Applicant: AGIOS PHARMACEUTICALS, INC, Cambridge, MA (US)

(72) Inventors: Jonathan Hurov, Cambridge, MA (US); Sung Eun Choe, Lexington, MA (US); Danielle Ulanet, Cambridge, MA (US)

(73) Assignee: Agios Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/444,807

(22) Filed: Feb. 28, 2017

(65) Prior Publication Data

US 2017/0299593 A1  Oct. 19, 2017

Related U.S. Application Data

(63) Continuation of application No. 14/428,456, filed as application No. PCT/US2013/599967 on Sep. 16, 2013, now Pat. No. 9,618,514.

(60) Provisional application No. 61/805,512, filed on Mar. 26, 2013, provisional application No. 61/702,091, filed on Sep. 17, 2012.

(51) Int. Cl.

| C12Q 1/68 | (2018.01) |
| G01N 33/574 | (2006.01) |
| C12Q 1/6886 | (2018.01) |
| A61K 38/50 | (2006.01) |
| A61K 31/433 | (2006.01) |

(52) U.S. Cl.
CPC ..... *G01N 33/57423* (2013.01); *A61K 31/433* (2013.01); *A61K 38/50* (2013.01); *C12Q 1/6886* (2013.01); *C12Y 305/01002* (2013.01); *G01N 33/57407* (2013.01); *C12Q 2600/106* (2013.01); *C12Q 2600/158* (2013.01); *C12Y 305/01001* (2013.01); *G01N 2333/705* (2013.01); *G01N 2800/52* (2013.01)

(58) Field of Classification Search
None
See application file for complete search history.

(56) References Cited

U.S. PATENT DOCUMENTS

| 5,895,748 | A | 4/1999 | Johnson et al. |
| 5,997,866 | A | 12/1999 | Johnson et al. |
| 9,618,514 | B2 * | 4/2017 | Choe .......... C12O 1/6886 |
| 2002/0115698 | A1 | 8/2002 | Newcomb et al. |
| 2002/0142981 | A1 | 10/2002 | Horne et al. |
| 2003/0054985 | A1 | 3/2003 | Aaronson et al. |
| 2004/0023288 | A1 | 2/2004 | Ridder et al. |
| 2004/0038207 | A1 | 2/2004 | Orntoft |
| 2006/0211060 | A1 | 9/2006 | Haley et al. |
| 2009/0226396 | A1 | 9/2009 | Haley et al. |
| 2011/0182886 | A1 | 7/2011 | Hongo et al. |
| 2012/0141479 | A1 | 6/2012 | Witta et al. |
| 2012/0142028 | A1 | 6/2012 | Richardson et al. |
| 2012/0190565 | A1 | 7/2012 | Lisanti et al. |
| 2012/0220610 | A1 | 8/2012 | Cerione et al. |
| 2013/0331432 | A1 | 12/2013 | Stephanopoulos et al. |
| 2016/0008380 | A1 | 1/2016 | Raabe et al. |

FOREIGN PATENT DOCUMENTS

| DE | 2037257 A1 | 2/1972 |
| WO | 1994022842 A1 | 10/1994 |
| WO | 2006040569 A1 | 4/2006 |
| WO | 2008048967 A1 | 4/2008 |
| WO | 2011143160 A2 | 11/2011 |
| WO | 2011163332 A2 | 12/2011 |
| WO | 2012006506 A1 | 1/2012 |
| WO | 2012120428 A1 | 9/2012 |
| WO | 2012171337 A1 | 12/2012 |
| WO | 2013078123 A1 | 5/2013 |
| WO | 2013138790 A1 | 9/2013 |

OTHER PUBLICATIONS

Cao et al. "Tissue transglutaminase links TGF-b epithelial to mesenchymal transition and a stem cell phenotype in ovarian cancer," Oncogene, 2012, vol. 31, p. 2521-2534.

Kumar et al. "Tissue transglutaminase promotes drug resistance and invasion by inducing mesenchymal transition in mammary epitherlial cells," PLoS ONE, 2010, vol. 5, No. 10, e. 13390.

Lin et al. "Role of tissue transglutaminase 2 in the acquisition of a mesenchymal-like phenotype in highly invasive A431 tumor cells," Molecular Cancer, 2011, vol. 10, No. 87.

Extended European Search Report for PCT/US2013/059967 dated Jul. 18, 2016.

El-Asmar et al. "Studies on the mechanism of inhibition of tumor growth by the enzyme glutaminase," Cancer Research, 1966, vol. 26, p. 116-122.

Delabarre et al. "Full-length human glutaminase in complex with an allosteric inhibitor," Biochemistry, 2011, vol. 50, No. 50, p. 10764-10770.

Hands et al. "A convenient method for the preparation of 5-, 6-, and 7-azaindoles and their derivatives," Synthesis, 1996, p. 877-882.

Hoffman et al. "Imidazol-4,5-dicarbonsaure-derivate; n-alkyl-substituierte amide oligomethylenverbruckter bis-imidazol-4,5-dicarbonsauren," Zeitschrift Fur Chemie, 1997, vol. 17, No. 4, p. 138-139.

International Search Report and Written Opinion for PCT/CN2013/000294 dated Sep. 5, 2013.

International Search Report and Written Opinion for PCT/CN2013001428 dated Mar. 6, 2014.

International Search Report and Written Opinion for PCT/CN2014/073812 dated Dec. 24, 2014.

International Search Report and Written Opinion for PCT/US2013/59967 dated Sep. 16, 2013.

(Continued)

*Primary Examiner* — Ralph J Gitomer
(74) *Attorney, Agent, or Firm* — Goodwin Procter LLP

(57) ABSTRACT

Methods and kits for the selection, evaluation, and/or treatment of a patient having cancer with an inhibitor of a glutamine-utilizing enzyme or a glutamine-depleting agent, by evaluating E-cadherin or vimentin expression are disclosed.

20 Claims, 17 Drawing Sheets

(56) References Cited

OTHER PUBLICATIONS

International Search Report and Written Opinion for PCT/US2013/071212 dated Apr. 9, 2014.
International Search Report for PCT/CN2012/085023 dated Aug. 29, 2013.
International Search Report for PCT/US2015/021781 dated Jun. 22, 2015.
Kafkewitz et al. "Enzyme-induced asparagine and glutamine depletion and immune system function1-3," The American Journal of Clinical Nutrition, 1983, vol. 37, p. 1025-1030.
Kumar. "Synthesis and pharmacological evaluation of some novel imidazo[2,1-b][1,3,4]thiadiazole derivatives," Chinese Journal of Chemistry, 2010, vol. 28, No. 2, p. 250-254.
Kung et al. "11 glutamine synthetase is a genetic determinant of cell type-specific glutamine independence in breast epithelia," PLOS Genetics, 2011, vol. 7, No. 8, p. e1002229.
Majee. "Synthesis of thiosemicarbazides, triazoles, thiadiazoles, and oxadiazoles," Current Science, 1989, vol. 58, No. 21, p. 1198-1201.
Mukhina et al. "Di-(carbohydrazidomethyl)-sulfide, sulfoxide, and sulfone and their derivatives that correspond to it," Izvestiya Vysshikh Uchebnykh Zavedeniy SSSR. Khimiya Ikhimicheskaya Tekhnologiya, 1996, vol. 4, p. 586-590.
Panwar et al. "Studies on some bioactive 1,1-bis(2-bensylidene-5-aryliden-1,3-thiadiazolidin-4-one)cyclopropane," Journal of the Korean Chemical Society, 2011, vol. 55, No. 6, p. 994-999.
Partial Search Report from EP 13837050 dated Mar. 8, 2016.
PubChem. CID 13735314. Feb. 9, 2007.
PubChem. CID 22812110. Dec. 5, 2007.
PubChem. CID 59841146. Aug. 20, 2012.
PubChem. CID 66760293. Nov. 30, 2012.
Ram et al. "Bis heterocycles as potential chemotherapeutic agents. X. Synthesis of bis(4-arylthiosemicarbazido)-, bis(2-arylamino-1,3,4-thiadiazol-5-yl) and bis(4-aryl-1,2,4-triazolin-3-thione-5-yl)pentanes and related compounds," Journal of Heterocyclic Chemistry, 1990, vol. 27, p. 351-355.
Ram et al. "Bis-heterocyclies. Part III. Synthesis of teetramethylene-3,3-di-1,2,4-triazoles and tetramethylene-2,2-di-1,3,4-thiadiazoles," Recueil des Travaux Chimiques des Pays-Bas, Jounal of the Royal Netherlands Chemical Society, 1977, vol. 96, No. 7-8, p. 181-182.
Robinson et al. "Novel mechanism of inhibition of rat kidney-type glutaminase by bis-2-(5-phenylacetamido-1,2,4-thiadiazol-2-yl)ethyl sulfide (BPTES)," Biochemical Journal, 2007, vol. 406, No. 3, p. 407-414.
Sharba et al. "Synthesis of thiadiazoles and 1,2,4-triazoles dervied from cyclopropane dicarboxylic acid," Molecules, 2005, vol. 10, No. 9, p. 1153-1160.
Shukla et al. "Design, synthesis, and pharmacological evaluation of bis-2-(5-phenylacetamido-1,2,4-thiadiozol-2-yl)ethyl sulfide 3 (BPTES) analogs as glutaminase inhibitors," Journal of Medicinal Chemistry, 2012, vol. 55, No. 2, p. 10551-10563.
Singh et al. "Selection of metastatic breast cancer cells based on adaptability of their metabolic state," PLOS One, 2012, vol. 7, No. 5, p. e36510.
Srivasta et al. "Synthesis and fungicidal activity of some new bis-heterocycles," Indian Chemical Society, 2011, vol. 68, p. 365-367.
Thangavelu et al. "Structural basis for the allosteric inhibitory mechanism of human kidney-type glutaminase (KGA) and its regulation by Raf-Mek-Erk signaling in cancer cell metabolism," Proceedings of the National Academy of Sciences, 2012, vol. 109, No. 20, p. 7705-7710.
Wise et al. "11 Glutamine addiction: A new therapeutic target in cancer," Trends in Biochemical Sciences, 2010, vol. 35, No. 8, p. 427-433.

\* cited by examiner

| Rank | Pathway | pValue | Ratio |
|---|---|---|---|
| 1 | Development_WNT signaling pathway. Part 2 | 4.737E-07 | 7 53 |
| 2 | Immune response_IL-1 signaling pathway | 2.706E-06 | 6 44 |
| 3 | Immune response_Murine NKG2D signaling | 3.820E-05 | 5 42 |
| 4 | Immune response_CD16 signaling in NK cells | 3.824E-05 | 9 89 |
| 5 | Immune response_Function of MEF2 in T lymphocytes | 8.982E-05 | 5 50 |
| 6 | Immune response_NFAT in immune response | 9.887E-05 | 5 51 |
| 7 | Development_Role of HDAC and calcium/calmodulin-dependent kinase (CaMK) in control of skeletal myogenesis | 1.303E-04 | 6 54 |
| 8 | Immune response_Fc epsilon RI pathway | 1.424E-04 | 5 55 |
| 9 | Development_Gastrin in cell growth and proliferation | 2.517E-04 | 5 62 |
| 10 | Development_NOTCH1-mediated pathway for NF-kB activity modulation | 2.517E-04 | 4 34 |
| 11 | G-protein signaling_G-Protein alpha-12 signaling pathway | 3.510E-04 | 4 37 |
| 12 | Immune response_Human NKG2D signaling | 3.824E-04 | 4 38 |
| 13 | Immune response_PIP3 signaling in B lymphocytes | 5.745E-04 | 4 42 |
| 14 | Development_GDNF family signaling | 8.146E-04 | 4 46 |
| 15 | Development_TGF-beta-dependent induction of EMT via MAPK | 8.042E-04 | 4 47 |
| 16 | Development_VEGF signaling via VEGFR2 - generic cascades | 1.026E-03 | 5 84 |
| 17 | Immune response_IL-2 activation and signaling pathway | 1.036E-03 | 4 49 |
| 18 | G-protein signaling_Cross-talk between Ras-family GTPases | 1.170E-03 | 3 23 |
| 19 | Immune response_CD28 signaling | 1.402E-03 | 4 54 |
| 20 | Immune response_BCR pathway | 1.403E-03 | 4 54 |
| 21 | G-protein signaling_Rap2B regulation pathway | 1.712E-03 | 2 7 |
| 22 | Immune response_TREM1 signaling pathway | 2.075E-03 | 4 59 |
| 23 | Development_Regulation of epithelial-to-mesenchymal transition (EMT) | 2.708E-03 | 4 64 |
| 24 | Cell adhesion_Role of CDK5 in cell adhesion | 2.804E-03 | 2 9 |
| 25 | Hypoxia-induced EMT in cancer and fibrosis | 2.808E-03 | 2 9 |

FIG. 2

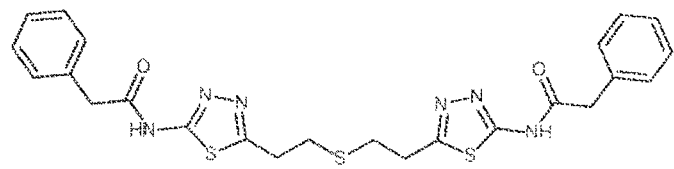
BPTES
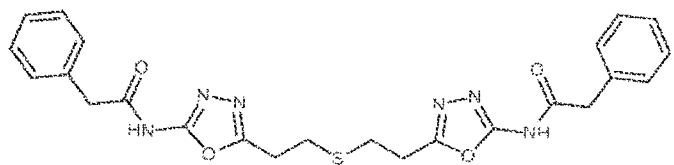
Compound I
FIG. 7

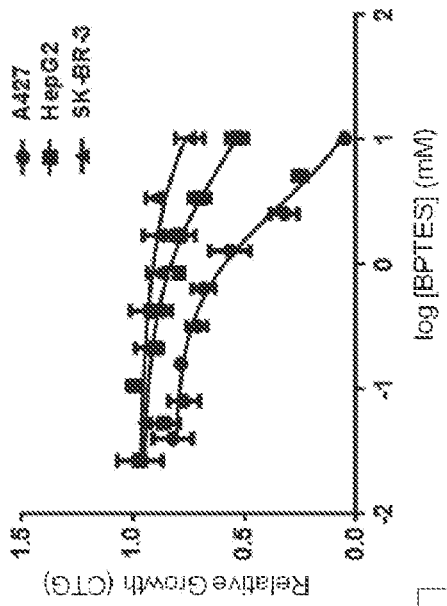
FIG. 8C
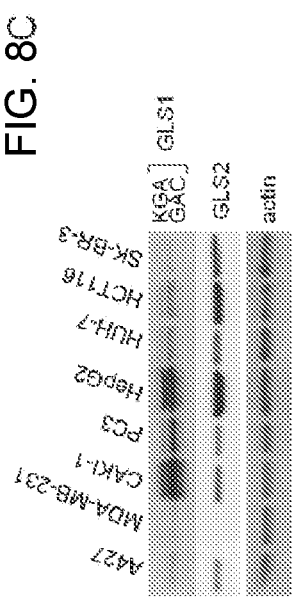
FIG. 8A
| Cell Line | Origin | Absolute IC$_{50}$(uM) | Avg max % inhibition |
|---|---|---|---|
| A427 | NSCLC | 2.6 | 84 |
| MDA-MB-231 | breast | 4.4 | 69 |
| Caki-1 | renal | 5.0 | 67 |
| PC3 | prostate | 7.2 | 54 |
| HepG2 | liver | >10 | 42 |
| Huh-7 | liver | >10 | 36 |
| HCT116 | colorectal | >10 | 30 |
| SK-BR-3 | breast | >10 | 30 |
FIG. 8B

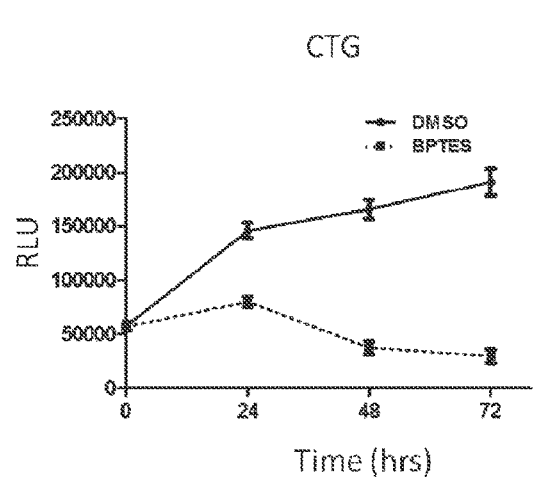 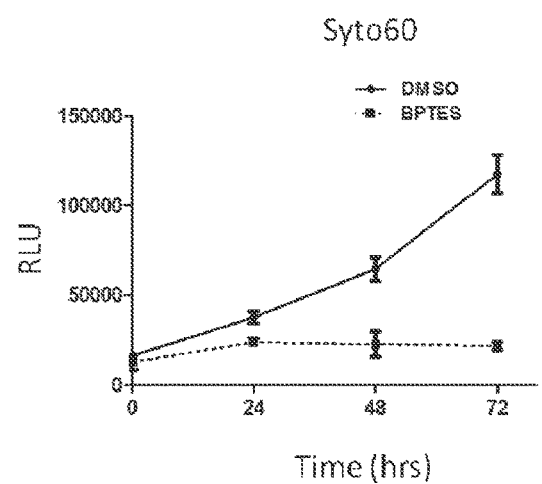
FIG. 9A  FIG. 9B

METHODS OF EVALUATING PATIENTS USING E-CADHERIN OR VIMENTIN

CLAIM OF PRIORITY

This application is a continuation of U.S. Ser. No. 14/428,456 filed Mar. 16, 2015, which is a national stage application under 35 U.S.C. § 371 of International Application No. PCT/US2013/059967, filed Sep. 16, 2013, published as International Publication No. WO2014/043633 on Mar. 20, 2014 which claims priority from U.S. Ser. No. 61/702,091, filed Sep. 17, 2012, and U.S. Ser. No. 61/805,512, filed Mar. 26, 2013, each of which is incorporated herein by reference in its entirety.

BACKGROUND OF THE INVENTION

Cancer cells rely primarily on glycolysis to generate cellular energy and biochemical intermediates for biosynthesis of lipids and nucleotides, while the majority of "normal" cells in adult tissues utilize aerobic respiration. This fundamental difference in cellular metabolism between cancer cells and normal cells is termed the Warburg Effect. As a result of this difference, pyruvate generated via the glycolytic pathway is converted to lactic acid, rather than being used to acetyl-CoA and eventually, the citrate utilized in a normal citric acid cycle. To compensate for these energetic changes and to maintain a citric acid cycle, cancer cells rely on glutamine metabolism which is achieved through, for an example, an elevation of glutaminase activity. Exploitation of this phenomenon can be achieved by inhibition of glutamine utilizing enzymes, for example, the elevated glutaminase activity. Phosphate-activated renal glutaminase (GLS1/KGA) has been shown to promote cancer cell proliferation at least in part via anaplerosis of the tricarboxylic acid cycle (TCA). GLS1 is not frequently mutated or amplified in tumors, making the selection of patients for treatment with a GLS inhibitor difficult. Therefore methods are needed to evaluate and/or select patients for treatment with GLS inhibitors.

SUMMARY OF INVENTION

In one aspect, the methods described herein provide, inter alia, methods of treating a patient having cancer, the method comprising: optionally, acquiring a patient sample; acquiring an evaluation of or evaluating the sample, wherein the sample is characterized by i) a low level of E-cadherin expression compared to a reference standard or ii) a high level of vimentin expression compared to a reference standard; and administering to the patient in need thereof a therapeutically effective amount of an inhibitor of a glutamine-utilizing enzyme (e.g, glutaminase) or a glutamine-depleting agent.

In one aspect, the methods described herein provide, inter alia, methods of treating a patient having cancer, the method comprising: optionally, acquiring a patient sample; acquiring an evaluation of or evaluating the sample, wherein the sample is characterized as a mesenchymal cell compared to a reference standard; and administering to the patient in need thereof a therapeutically effective amount of an inhibitor of a glutamine-utilizing enzyme (e.g. glutaminase) or a glutamine-depleting agent. In some embodiments the characterized as a mesenchymal cell is compared to a reference standard, wherein the reference standard is the characterized as a mesenchymal cell as described on any one of the following references: (Yauch et al., (2005) Clin Cancer Res 11:24; Savagner et al., (2010) Ann Oncol. 21(suppl 7): vii89; Thiery et al., (2002) Nature Reviews Cancer 2(6):442).

In one aspect, the methods described herein provide, inter alia, methods of treating a patient having cancer, the method comprising: optionally, acquiring a patient sample; acquiring an evaluation of or evaluating the sample, wherein the sample is characterized by i) a low level of E-cadherin expression compared to a reference standard or ii) a high level of vimentin expression compared to a reference standard; and administering to the patient in need thereof a therapeutically effective amount of a glutamine-depleting agent.

In one aspect, the methods described herein provide, inter alia, methods of treating a patient having cancer, the method comprising: optionally, acquiring a patient sample; acquiring an evaluation of or evaluating the sample, wherein the sample is characterized by i) a low level of E-cadherin expression compared to a reference standard or ii) a high level of vimentin expression compared to a reference standard; and administering to the patient in need thereof a therapeutically effective amount of an inhibitor of a glutamine-utilizing enzyme (e.g., glutaminase (e.g., GLS1 or glutaminase C (GAC))). In some embodiments, the sample is characterized by low or decreased levels of pyruvate carboxylase expression compared to a reference standard. In some embodiments, the sample is characterized by a decreased capacity for oxidative phosphorylation compared to a reference standard. In some embodiments, the sample is characterized by a decreased capacity to respond to mitochondrial stress compared to a reference standard. In some embodiments, the sample is characterized by a decreased use of endogenous pyruvate for cellular respiration. In some embodiments, the sample is characterized by a dependence on glutamine for cellular respiration.

In some embodiments, the sample is characterized by i) a low level of E-cadherin expression compared to a reference standard and ii) a high level of vimentin expression compared to a reference standard. In some embodiments, the sample is characterized or further characterized by low or decreased levels of pyruvate carboxylase expression compared to a reference standard. In some embodiments, the sample is characterized or further characterized by decreased capacity for oxidative phosphorylation compared to a reference standard. In some embodiments, the sample is characterized or further characterized by a decreased capacity to respond to mitochondrial stress compared to a reference standard. In some embodiments, the sample is characterized or further characterized by a decreased use of endogenous pyruvate for cellular respiration. In some embodiments, the sample is characterized or further characterized by a dependence on glutamine for cellular respiration.

In some embodiments the level of E-cadherin expression is compared to a reference standard, wherein the reference standard is the level of E-cadherin expression in an epithelial cell as characterized on any one of the following references: (Yauch et al., (2005) Clin Cancer Res 11:24; Savagner et al., (2010) Ann Oncol. 21(suppl 7): vii89; Thiery et al., (2002) Nature Reviews Cancer 2(6):442). In some embodiments, the level of E-cadherin expression is measured by the evaluation of the level of RNA that encodes E-cadherin. In some embodiments, the level of E-cadherin expression is evaluated by the level of E-cadherin protein expression. In some embodiments the level of E-cadherin expression is at least 5, 10, 15, 20, 25, 30, 40, 50, 60, 70, 80, or 90% less than the reference standard. In some embodiments the level of E-cadherin expression is at least a 1.5, 2, 5, 10, 15, 20, 25, 50, 75, 100 fold decrease in expression compared to the reference standard.

In some embodiments the level of vimentin expression is compared to a reference standard, wherein the reference standard is the level of vimentin expression in an epithelial cell as characterized on any one of the following references: (Yauch et al., (2005) Clin Cancer Res 11:24; Savagner et al., (2010) Ann Oncol. 21(suppl 7): vii89; Thiery et al., (2002) Nature Reviews Cancer 2(6):442). In some embodiments, the level of vimentin expression is measured by the evaluation of the level of RNA that encodes vimentin. In some embodiments, the level of vimentin expression is evaluated by the level of vimentin protein expression. In some embodiments the level of vimentin expression is at least 5, 10, 15, 20, 25, 30, 40, 50, 60, 70, 80, or 90% greater than the reference standard. In some embodiments the level of vimentin expression is at least a 1.5, 2, 5, 10, 15, 20, 25, 50, 75, 100 fold increase in expression compared to the reference standard.

In some embodiments the level of pyruvate carboxylase expression is low or decreased compared to a reference standard, wherein the reference standard is the level of pyruvate carboxylase expression in an epithelial cell as characterized on any one of the following references: (Yauch et al., (2005) Clin Cancer Res 11:24; Savagner et al., (2010) Ann Oncol. 21(suppl 7): vii89; Thiery et al., (2002) Nature Reviews Cancer 2(6):442). In some embodiments, the level of pyruvate carboxylase expression is high or increased compared to the reference standard. In some embodiments, the level of pyruvate carboxylase expression is measured by the evaluation of the level of RNA that encodes pyruvate carboxylase. In some embodiments, the level of vimentin expression is evaluated by the level of pyruvate carboxylase protein expression. In some embodiments the level of pyruvate carboxylase expression is at least 5, 10, 15, 20, 25, 30, 40, 50, 60, 70, 80, or 90% greater than the reference standard. In some embodiments the level of pyruvate carboxylase expression is at least a 1.5, 2, 5, 10, 15, 20, 25, 50, 75, 100 fold increase in expression compared to the reference standard.

In some embodiments, the glutamine-depleting agent is an asparaginase (such as Elspar® (Merck), Oncaspar® (Sigma Tau/Enzon), and Erwinaze® (EUSA)), a glutaminase including pegylated forms (such as those described in U.S. Pat. No. 7,052,689 and U.S. Pat. No. 6,312,939, content of each is incorporated herein by reference), or GlutaDon (as described in US2009/0169537, content of which is incorporated herein by reference).

In some embodiments, the glutaminase (GLS) inhibitor is bis-2-(5-phenylacetamido-1,2,4-thiadiazol-2-yl)ethyl sulfide (BPTES). In some embodiments, the GLS inhibitors are as described in U.S. Pat. No. 6,451,828; WO2010/111504 (US2012/0220610); WO2012/034123; WO2011/143160; U.S. Pat. No. 5,552,427 and WO2010/033871, the content of each is incorporated herein by reference. In some embodiments, the glutamine-utilizing enzyme inhibitor is as described in U.S. Pat. No. 7,714,007 (the content of which is incorporated herein by reference), such as an amidotransferase inhibitor, long chain fatty acid, 6-diazo-5-oxo-L-norleucine (DON), N-ethylmaleimide (NEM), p-chloromercuriphenylsulfonate (pCMPS), L-2-amino-4-oxo-5-chloropentoic acid, DON plus o-carbamoyl-L-serine, acivicin [(alphaS,5S)-alpha-amino-3-chloro-4,5-dihydro-5-isoxazoleacetic acid], azaserine, palmitoyl coenzyme A (CoA), stearoyl CoA, bromothymol blue, and dicoumarol.

In some embodiments, the inhibitor of a glutamine-utilizing enzyme (e.g, glutaminase) or a glutamine-depleting agent is administered in combination with a second therapeutic agent. In some embodiments, the second therapeutic agent is a chemotherapeutic agent. In some embodiments the second therapeutic agent is an epidermal growth factor receptor (EGFR) inhibitor, e.g., cetuximab, panitumumab, gefitinib, erlotinib, nimotuzamab, matuzamab, zalutumumab, or lapatinib.

In some embodiments, the cancer is lung cancer. In some embodiments the cancer is non-small cell lung cancer. In some embodiments the cancer is breast cancer. In some embodiments the cancer is hepatocellular carcinoma. In some embodiments the caner is osteosarcoma, lipomas, chondrosarcoma, or mesothelioma. In some embodiments the cancer is osteosarcoma. In some embodiments the cancer is lipomas. In some embodiments the cancer is chondrosarcoma. In some embodiments the cancer is mesothelioma.

In another aspect, the methods described herein provide, inter alia, methods evaluating a patient having cancer for treatment with an inhibitor of glutamine utilizing enzyme (e.g., a GLS (e.g., GLS1 or GAC) inhibitor) or a glutamine-depleting agent, the method comprising: optionally, acquiring a patient sample; evaluating the sample, wherein the sample is characterized by i) a low level of E-cadherin expression compared to a reference standard or ii) a high level of vimentin expression compared to a reference standard; and determining to treat the patient with an inhibitor of a glutamine utilizing enzyme (e.g., a GLS (e.g., GLS1 or GAC) inhibitor) or a glutamine-depleting agent.

In some embodiments, the sample is characterized by low or decreased levels of pyruvate carboxylase expression compared to a reference standard. In some embodiments, the sample is characterized by a decreased capacity for oxidative phosphorylation compared to a reference standard. In some embodiments, the sample is characterized by a decreased capacity to respond to mitochondrial stress compared to a reference standard. In some embodiments, the sample is characterized by a decreased use of endogenous pyruvate for cellular respiration. In some embodiments, the sample is characterized by a dependence on glutamine for cellular respiration.

In some embodiments the level of E-cadherin expression is compared to a reference standard, wherein the reference standard is the level of E-cadherin expression in an epithelial cell as characterized on any one of the following references: (Yauch et al., (2005) Clin Cancer Res 11:24; Savagner et al., (2010) Ann Oncol. 21(suppl 7): vii89; Thiery et al., (2002) Nature Reviews Cancer 2(6):442). In some embodiments, the level of E-cadherin expression is low, decreased, or absent compared to the reference standard. In some embodiments, the level of E-cadherin expression is measured by the evaluation of the level of RNA that encodes E-cadherin. In some embodiments, the level of E-cadherin expression is evaluated by the level of E-cadherin protein expression. In some embodiments the level of E-cadherin expression is at least 5, 10, 15, 20, 25, 30, 40, 50, 60, 70, 80, or 90% less than the reference standard. In some embodiments the level of E-cadherin expression is at least a 1.5, 2, 5, 10, 15, 20, 25, 50, 75, 100 fold decrease in expression compared to the reference standard.

In some embodiments the level of vimentin expression is compared to a reference standard, wherein the reference standard is the level of vimentin expression in an epithelial cell as characterized on any one of the following references: (Yauch et al., (2005) Clin Cancer Res 11:24; Savagner et al., (2010) Ann Oncol. 21(suppl 7): vii89; Thiery et al., (2002)

Nature Reviews Cancer 2(6):442). In some embodiments, the level of vimentin expression is measured by the evaluation of the level of RNA that encodes vimentin. In some embodiments, the level of vimentin expression is evaluated by the level of vimentin protein expression. In some embodiments the level of vimentin expression is at least 5, 10, 15, 20, 25, 30, 40, 50, 60, 70, 80, or 90% greater than the reference standard. In some embodiments the level of vimentin expression is at least a 1.5, 2, 5, 10, 15, 20, 25, 50, 75, 100 fold increase in expression compared to the reference standard.

In some embodiments the level of pyruvate carboxylase expression is low or decreased compared to a reference standard, wherein the reference standard is the level of pyruvate carboxylase expression in an epithelial cell as characterized on any one of the following references: (Yauch et al., (2005) Clin Cancer Res 11:24; Savagner et al., (2010) Ann Oncol. 21(suppl 7): vii89; Thiery et al., (2002) Nature Reviews Cancer 2(6):442). In some embodiments, the level of pyruvate carboxylase expression is high or increased compared to the reference standard. In some embodiments, the level of pyruvate carboxylase expression is measured by the evaluation of the level of RNA that encodes pyruvate carboxylase. In some embodiments, the level of vimentin expression is evaluated by the level of pyruvate carboxylase protein expression. In some embodiments the level of pyruvate carboxylase expression is at least 5, 10, 15, 20, 25, 30, 40, 50, 60, 70, 80, or 90% greater than the reference standard. In some embodiments the level of pyruvate carboxylase expression is at least a 1.5, 2, 5, 10, 15, 20, 25, 50, 75, 100 fold increase in expression compared to the reference standard.

In some embodiments, the cancer is lung cancer. In some embodiments the cancer is non-small cell lung cancer. In some embodiments the cancer is breast cancer. In some embodiments the cancer is hepatocellular carcinoma. In some embodiments the caner is osteosarcoma, lipomas, chondrosarcoma, or mesothelioma. In some embodiments the cancer is osteosarcoma. In some embodiments the cancer is lipomas. In some embodiments the cancer is chondrosarcoma. In some embodiments the cancer is mesothelioma.

In some embodiments, subsequent to the evaluation, the method further comprises selecting an inhibitor of a glutamine utilizing enzyme (e.g., a GLS (e.g., GLS1 or GAC) inhibitor) for treatment of the patient.

In some embodiments, subsequent to the evaluation, the method further comprises selecting a glutamine-depleting agent for treatment of the patient.

In some embodiments, subsequent to the evaluation, the method further comprises selecting a GLS inhibitor for treatment of the patient.

In one aspect, a kit or product comprising a means to assay the level of gene expression of E-cadherin and/or vimentin and/or pyruvate carboxylase is provided. In some embodiment, the kit or product comprises an agent capable of interacting with a gene expression product of E-cadherin. In some embodiment, the kit or product comprises an agent capable of interacting with a gene expression product of vimentin. In some embodiment, the kit or product comprises an agent capable of interacting with a gene expression product of E-cadherin and an agent capable of interacting with a gene expression product of vimentin. In some embodiments the agent is an antibody. In some embodiments the agent is an oligonucleotide. In some embodiments the gene expression product is a RNA molecule. In some embodiment the gene expression product is a mRNA molecule. In some embodiment the gene expression product is a polypeptide or protein.

In one aspect, the methods described herein provide, inter alia, methods of treating a patient having cancer, the method comprising: optionally, acquiring a patient sample; acquiring an evaluation of or evaluating the sample, wherein the sample is characterized by i) a decreased capacity for oxidative phosphorylation compared to a reference standard or ii) a decreased capacity to respond to mitochondrial stress compared to a reference standard or iii) a decreased use of endogenous pyruvate for cellular respiration or iv) a dependence on glutamine for cellular respiration; and administering to the patient in need thereof a therapeutically effective amount of an inhibitor of a glutamine-utilizing enzyme (e.g, glutaminase) or a glutamine-depleting agent.

In one aspect, the methods described herein provide, inter alia, methods of treating a patient having cancer, the method comprising: optionally, acquiring a patient sample; acquiring an evaluation of or evaluating the sample, wherein the sample is characterized by i) a decreased capacity for oxidative phosphorylation compared to a reference standard or ii) a decreased capacity to respond to mitochondrial stress compared to a reference standard or iii) a decreased use of endogenous pyruvate for cellular respiration or iv) a dependence on glutamine for cellular respiration; and administering to the patient in need thereof a therapeutically effective amount of a glutamine-depleting agent.

In one aspect, the methods described herein provide, inter alia, methods of treating a patient having cancer, the method comprising: optionally, acquiring a patient sample; acquiring an evaluation of or evaluating the sample, wherein the sample is characterized by i) a decreased capacity for oxidative phosphorylation compared to a reference standard or ii) a decreased capacity to respond to mitochondrial stress compared to a reference standard or iii) a decreased use of endogenous pyruvate for cellular respiration or iv) a dependence on glutamine for cellular respiration; and administering to the patient in need thereof a therapeutically effective amount of an inhibitor of a glutamine-utilizing enzyme (e.g., glutaminase (e.g., GLS1 or glutaminase C (GAC))).

In some embodiments the capacity for oxidative phosphorylation is low or decreased compared to a reference standard, wherein the reference standard is the capacity for oxidative phosphorylation in an epithelial cell as characterized on any one of the following references: (Yauch et al., (2005) Clin Cancer Res 11:24; Savagner et al., (2010) Ann Oncol. 21(suppl 7): vii89; Thiery et al., (2002) Nature Reviews Cancer 2(6):442).

In some embodiments the capacity to respond to mitochondrial stress is low or decreased compared to a reference standard, wherein the reference standard is the capacity to respond to mitochondrial stress in an epithelial cell as characterized on any one of the following references: (Yauch et al., (2005) Clin Cancer Res 11:24; Savagner et al., (2010) Ann Oncol. 21(suppl 7): vii89; Thiery et al., (2002) Nature Reviews Cancer 2(6):442).

In some embodiments the use of endogenous pyruvate for cellular respiration is low or decreased compared to a reference standard, wherein the reference standard is the use of endogenous pyruvate for cellular respiration in an epithelial cell as characterized on any one of the following references: (Yauch et al., (2005) Clin Cancer Res 11:24; Savagner et al., (2010) Ann Oncol. 21(suppl 7): vii89; Thiery et al., (2002) Nature Reviews Cancer 2(6):442).

In some embodiments the dependence on glutamine for cellular respiration is low or decreased compared to a reference standard, wherein the reference standard is the dependence on glutamine for cellular respiration in an epithelial cell as characterized on any one of the following references: (Yauch et al., (2005) Clin Cancer Res 11:24; Savagner et al., (2010) Ann Oncol. 21(suppl 7): vii89; Thiery et al., (2002) Nature Reviews Cancer 2(6):442).

In some embodiments, the cancer is lung cancer. In some embodiments the cancer is non-small cell lung cancer. In some embodiments the cancer is breast cancer. In some embodiments the cancer is hepatocellular carcinoma. In some embodiments the caner is osteosarcoma, lipomas, chondrosarcoma, or mesothelioma. In some embodiments the cancer is osteosarcoma. In some embodiments the cancer is lipomas. In some embodiments the cancer is chondrosarcoma. In some embodiments the cancer is mesothelioma.

In some embodiments, subsequent to the evaluation, the method further comprises selecting an inhibitor of a glutamine utilizing enzyme (e.g., a GLS (e.g., GLS1 or GAC) inhibitor) for treatment of the patient.

In some embodiments, subsequent to the evaluation, the method further comprises selecting a glutamine-depleting agent for treatment of the patient.

In some embodiments, subsequent to the evaluation, the method further comprises selecting a GLS inhibitor for treatment of the patient.

BRIEF DESCRIPTION OF THE DRAWINGS

FIG. 2 depicts the top 25 pathways associated with either BPTES sensitivity or resistance and the correlation with the effect of BPTES on cell growth ($\mu/\mu_{max}$). The shaded rows depict 4 pathways related to the epithelial-mesenchymal transition (ranks 1, 15, 23, 25).

FIG. 7 depicts the structures of BPTES and Compound I.

FIGS. 8A-8C depict the GLS1 dependence in selected cancer cell lines. FIG. 8A depicts a western blot analysis of GLS1 and GLS2 protein levels in indicated cell lines. KGA and GAC alternative splice variants are indicated. FIG. 8B depicts cell lines were assayed for sensitivity to BPTES treatment in a 72 hr proliferation assay using CellTiter-Glo in 96-well format. The tissue of origin, average $IC_{50}$ and percent inhibition of growth at the maximum dose of BPTES is reported. FIG. 8C depicts representative growth curves with BPTES treatment from indicated cell lines. Results are representative of three independent experiments with the mean and standard deviation (SD) indicated (Note: BPTES has poor aqueous solubility. Dosing cells above 10 mM results in precipitation of the compound).

FIGS. 9A-9B are line graphs depicting the comparison of two different methods of viability measurement. Growth of A427 cells treated with 8 mM BPTES measured by FIG. 9A CellTiter-Glo and FIG. 9B Syto60. At 72 hrs decreases in ATP levels measured by CellTiter-Glo are equivalent to decreases in cell density measured by Syto60 staining. Equivalent A427 cells were plated into 96 well plates and treated with DMSO or 8 mM BPTES. CellTiter-Glo and Syto60 measurements were taken at 0, 24, 48, and 72 hours post drug addition.

FIG. 10A shows BPTES treated cells indicating growth of drug treated cells relative to DMSO treated FIG. 10B shows cells treated with inactive analogue (Compound I) indicating growth of drug treated cells relative to DMSO treated. Results are representative of three independent experiments with mean and standard deviation indicated in FIG. 10C and FIG. 10D) Measurement of isotopomer labeled $^{13}C(5)$-Glu (FIG. 10C) or $^{13}C(4)$-Asp (FIG. 10D) from cells treated for 4 hr with BPTES or with inactive analogue Compound I. Results are the mean of three replicates with the standard deviation indicated. Calculated p-values from student t-test, * ($3\times10^{-8}$), ** ($10^{-9}$), # ($10^{-7}$), ## ($2\times10^{-6}$).

FIG. 11A shows BPTES treated cells indicating growth of drug treated cells relative to DMSO (FIG. 11B) Cells treated with inactive analogue (Compound I) indicating growth of drug treated cells relative to DMSO. Results are representative of three independent experiments with mean and standard deviation indicated (FIG. 11C and FIG. 11D) Measurement of isotopomer labeled $^{13}C(5)$-Glu (FIG. 11C) or $^{13}C(4)$-Asp (FIG. 11D) from cells treated for 4 hr with BPTES or with inactive analogue Compound I. Results are the mean of three replicates with the standard deviation indicated. Calculated p-values from student t-test, * ($3\times10^{-5}$), ** ($7\times10^{-10}$), # ($3\times10^{-5}$), ## ($5\times10^{-7}$).

FIG. 14A depicts an immunoblot for GLS1 expression in normal human tissues. FIG. 14B depicts an immunoblot for GLS2 expression in normal human tissues.

FIG. 15A Intracellular ATP and FIG. 15B Glutamate levels remaining after 24 hr treatment with 10 mM BPTES in 15 tumor cell lines. Sensitivity of cell lines plotted on the x-axis range from 96%-1% inhibition in a 72 hr viability assay, in order from left to right. Results are plotted as average and standard deviation of 3 independent experiments. Pearson correlation coefficient for ATP/growth inhibition=0.79, Glutamate/growth inhibition=0.71 (p=0.0002 and p=0.002, respectively)

DETAILED DESCRIPTION

Figure 1:
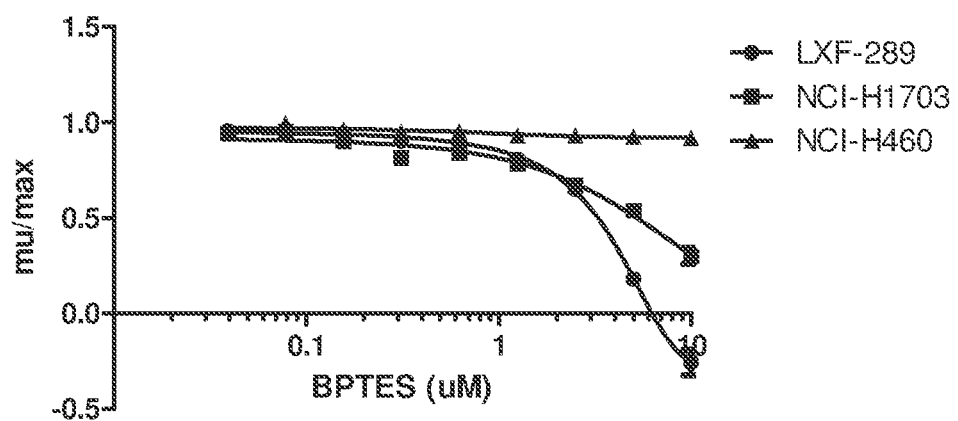
FIG. 1 depicts the growth response curves of three non-small cell lung cancer cell lines (LXF-289; NCI-H1703; NCI-H460) treated with varying concentrations of the GLS inhibitor BPTES.

Certain terms are first defined. Additional terms are defined throughout the specification.

"Acquire" or "acquiring" as the terms are used herein, refer to obtaining possession of a physical entity, or a value, e.g., a numerical value, by "directly acquiring" or "indirectly acquiring" the physical entity or value. "Directly acquiring" means performing a process (e.g., performing a synthetic or analytical method) to obtain the physical entity or value. "Indirectly acquiring" refers to receiving the physical entity or value from another party or source (e.g., a third party laboratory that directly acquired the physical entity or value). Directly acquiring a physical entity includes performing a process that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent.

"Acquiring a sample" as the term is used herein, refers to obtaining possession of a sample, e.g., a tissue sample or nucleic acid sample, by "directly acquiring" or "indirectly acquiring" the sample. "Directly acquiring a sample" means performing a process (e.g., performing a physical method such as a surgery or extraction) to obtain the sample. "Indirectly acquiring a sample" refers to receiving the sample from another party or source (e.g., a third party laboratory that directly acquired the sample). Directly acquiring a sample includes performing a process that includes a physical change in a physical substance, e.g., a starting material, such as a tissue, e.g., a tissue in a human patient or a tissue that has was previously isolated from a patient. Exemplary changes include making a physical entity from a starting material, dissecting or scraping a tissue; separating or purifying a substance (e.g., a sample tissue or a nucleic acid sample); combining two or more separate entities into a mixture; performing a chemical reaction that includes breaking or forming a covalent or non-covalent bond. Directly acquiring a sample includes performing a process that includes a physical change in a sample or another substance, e.g., as described above.

As used herein a "low" of E-cadherin expression compared to a reference standard refers a low, decreased, or absent level of E-cadherin expression compared to the level of E-cadherin expression in an epithelial cell as characterized by methods known in the art, e.g., on any one of the following references: (Yauch et al., (2005) Clin Cancer Res 11:24; Savagner et al., (2010) Ann Oncol. 21(suppl 7): vii89; Thiery et al., (2002) Nature Reviews Cancer 2(6):442).

As used herein, a "high" level of vimentin compared to a reference standard refers to a high or increased level of vimentin expression compared to the level of expression of vimentin in an epithelial cell as characterized by methods known in the art, e.g., on any one of the following references: (Yauch et al., (2005) Clin Cancer Res 11:24; Savagner et al., (2010) Ann Oncol. 21(suppl 7): vii89; Thiery et al., (2002) Nature Reviews Cancer 2(6):442).

As used herein, a "low" or "decreased", level of pyruvate carboxylase expression compared to a reference standard refers to a low, decreased, or absent level of E-cadherin expression compared to the level of E-cadherin expression in an epithelial cell as characterized by methods known in the art, e.g., on any one of the following references: (Yauch et al., (2005) Clin Cancer Res 11:24; Savagner et al., (2010) Ann Oncol. 21(suppl 7): vii89; Thiery et al., (2002) Nature Reviews Cancer 2(6):442).

As used herein, a glutamine depleting agent means an agent that is capable of depleting glutamine (such as a glutamine depleting enzyme glutaminase) or degrades glutamine.

As used herein, a glutaminase inhibitor means an agent that affects the activity of the glutaminase enzyme, such as inhibitors that may affect binding of glutamine, glutamate or various cofactors to the enzyme (for example, a glutaminase inhibitor may block binding of the substrate glutamine to glutaminase, inhibit release of the product glutamate from glutaminase, or block cofactor binding and therefore slow the catalytic rate of the enzyme); or an agent that inhibits glutaminase production.

As used herein, "cancer" and "tumor" are synonymous terms. The term "cancer" or "tumor" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells may exist alone within an animal, or may be a non-tumorigenic cancer cell, such as a leukemia cell. The cells can possess characteristics typical of a mesenchymal cell, such as characterized on any one of the following references: (Yauch et al., (2005) Clin Cancer Res 11:24; Savagner et al., (2010) Ann Oncol. 21(suppl 7): vii89; Thiery et al., (2002) Nature Reviews Cancer 2(6):442).

As used herein, and unless otherwise specified, the terms "treat", "treating" and "treatment" contemplate an action that occurs while a patient is suffering from a cancer, which reduces the severity of the cancer or retards or slows the progression of the cancer.

As used herein, and unless otherwise specified, a "therapeutically effective amount" of a compound is an amount sufficient to provide a therapeutic benefit in the treatment a cancer, or to delay or minimize one or more symptoms associated with the cancer. A therapeutically effective amount of a compound means an amount of therapeutic agent, alone or in combination with other therapeutic agents, which provides a therapeutic benefit in the treatment a cancer. The term "therapeutically effective amount" can encompass an amount that improves overall therapy, reduces or avoids symptoms or causes of the cancer, or enhances the therapeutic efficacy of another therapeutic agent.

The term "patient" and "subject" are synonymous, and as used herein, refer to an animal, typically a human (i.e., a male or female of any age group, e.g., a pediatric patient or adult patient or other mammal, such as primates (e.g., cynomolgus monkeys, rhesus monkeys); commercially relevant mammals such as cattle, pigs, horses, sheep, goats, cats, and/or dogs; and/or birds, including commercially relevant birds such as chickens, ducks, geese, and/or turkeys, that will be or has been the object of treatment, observation, and/or experiment. When the term is used in conjunction with administration of a compound or drug, then the patient has been the object of treatment, observation, and/or administration of the compound or drug.

The methods described herein provide methods of evaluating and/or treating a patient having cancer, by evaluating a patient sample, wherein the sample is characterized by i) a low level of E-cadherin expression compared to a reference standard or ii) a high level of vimentin expression compared to a reference standard; and administering to the patient in need thereof a therapeutically effective amount of an inhibitor of glutamine-utilizing enzyme (e.g., glutaminase) or a glutamine-depleting agent.

Patient Sample

The terms "patient sample", "subject sample", and "sample" are used interchangeably herein. The patient sample can be a tissue, or bodily fluid, or bodily product. Tissue samples can include fixed, paraffin embedded, fresh, or frozen samples. For example, the tissue sample can include a biopsy, cheek swab. Exemplary tissues include lung, breast, brain, nervous tissue, kidney, ovary, thyroid, pancreas, colon, prostate, lymph node, skin, hair follicles and nails. Exemplary samples include samples derived from solid tumors. Exemplary bodily fluids include blood, plasma, urine, lymph, tears, sweat, saliva, semen, and cerebrospinal fluid. Exemplary bodily products include exhaled breath.

The tissue, fluid or product can be removed from the patient and analyzed. The evaluation can include one or more of: performing the analysis of the tissue, fluid or product; requesting analysis of the tissue fluid or product; requesting results from analysis of the tissue, fluid or product; or receiving the results from analysis of the tissue, fluid or product.

The sample tissue, fluid, or product can be analyzed for the expression level of a gene described herein, e.g., E-cadherin, vimentin, pyruvate carboxylase. The sample tissue, fluid, or product can be analyzed for the expression level of a protein described herein, e.g., E-cadherin, vimentin, pyruvate carboxylase. The sample tissue, fluid or product can further be analyzed for the level of gene expression of a gene or plurality of genes of a preselected signaling pathway or phenotypic pathway, e.g., the epithelial to mesenchymal transition pathway, E-cadherin pathway, vimentin pathway, or the pyruvate carboxylase pathway. The sample tissue, fluid or product can further be analyzed for the level of protein expression of a protein or plurality of proteins of a preselected signaling pathway or phenotypic pathway, e.g., the epithelial to mesenchymal transition pathway, E-cadherin pathway, vimentin pathway, or the pyruvate carboxylase pathway.

Methods of Evaluating Samples and/or Subjects

This section provides methods of analyzing samples and of analyzing patients.

The expression level of a gene described herein, e.g., E-cadherin, vimentin, pyruvate carboxylase; can be assessed using any of a wide variety of well known methods for detecting expression of a transcribed molecule, gene, protein, mRNA, genomic DNA, or cDNA. Gene expression can be measured or monitored by measure of a gene transcript, e.g., mRNA, by a measure of the quantity of a translated protein, or by a measure of gene product activity; any of which can be measured using standard techniques known to one of skill in the art. Non-limiting examples of such methods include nucleic acid hybridization methods, nucleic acid reverse transcription methods, nucleic acid amplification methods, immunological methods for detection of proteins, protein purification methods, protein function or activity assays.

E-Cadherin

The E-cadherin gene is located on human chromosome 16. E-cadherin is a classical cadherin of the cadherin superfamily. The encoded E-cadherin protein is a calcium dependent cell-cell adhesion glycoprotein comprised of five extracellular cadherin repeats, a transmembrane region and a highly conserved cytoplasmic tail. Mutations in this gene have been correlated with cancer, including gastric, breast, colorectal, thyroid and ovarian cancers. Loss of function of E-cadherin is contemplated to contribute to cancer progression by increasing proliferation, invasion, and/or metastasis. The ectodomain of this protein mediates bacterial adhesion to mammalian cells and the cytoplasmic domain is required for internalization. Identified E-cadherin transcript variants arise from mutation at consensus splice sites.

Vimentin

The vimentin gene is located on human chromosome 10 and encodes a member of the intermediate filament family of proteins. Intermediate filaments, along with microtubules and actin microfilaments, make up the cellular cytoskeleton, which helps maintain cell shape and integrity of the cytoplasm, as well as stabilizing cytoskeletal interactions. Vimentin also functions in mediating immune responses, control of the transport of low-density lipoprotein derived cholesterol from lysosomes to the sites of esterification, and as an organizer of a number of critical proteins involved in attachment, migration, and cell signaling.

Pyruvate Carboxylase (PC)

The PC gene is located on human chromosomes 11 and encodes the protein pyruvate carboxylase, which catalyzes the carboxylation of pyruvate to oxaloacetate. The active enzyme is a homotetramer arranged in a tetrahedron which is located exclusively in the mitochondrial matrix. Pyruvate carboxylase is involved in multiple cellular processes including gluconeogenesis, lipogenesis, insulin secretion and synthesis of the neurotransmitter glutamate. Mutations in this gene have been associated with pyruvate carboxylase deficiency. Alternatively spliced transcript variants with different 5' UTRs, but encoding the same protein, have been identified.

Nucleic Acid Molecules

The methods described herein can pertain to the evaluation of a sample for the expression of a gene described herein, e.g., E-cadherin, vimentin, pyruvate carboxylase; based on isolated nucleic acids which correspond to the gene described herein, e.g., the mRNA level of E-cadherin; the mRNA level of vimentin; the mRNA level of pyruvate carboxylase. As used herein, the term "nucleic acid" or "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded.

An "isolated" nucleic acid molecule is one which is separated from other nucleic acid molecules which are present in the natural source of the nucleic acid molecule. An "isolated" nucleic acid molecule can be free of sequences (such as protein-encoding sequences) which naturally flank the nucleic acid (i.e., sequences located at the 5' and 3' ends of the nucleic acid) in the genomic DNA of the organism from which the nucleic acid is derived. An "isolated" nucleic acid molecule, such mRNA, can be substantially free of other cellular material cellular material or other contaminating proteins from the cell or tissue source from which the nucleic acid is derived.

A nucleic acid molecule described herein can be isolated using standard molecular biology techniques and the sequence information available in database records known to those of skill in the art. Using all or a portion of such nucleic acid sequences, nucleic acid molecules described herein can be isolated using standard hybridization and cloning techniques (e.g., as described in Sambrook et al., ed., *Molecular Cloning: A Laboratory Manual, 2nd ed.*, Cold Spring Harbor Laboratory Press, Cold Spring Harbor, N.Y., 1989).

A nucleic acid molecule described herein can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule can be prepared by standard synthetic techniques, e.g., using an automated DNA synthesizer.

An isolated nucleic acid molecule can comprise a nucleic acid molecule which has a nucleotide sequence complementary to the nucleotide sequence of a nucleic acid corresponding to gene described herein, or to the nucleotide sequence of a nucleic acid encoding a protein which corresponds to the gene described herein. A nucleic acid molecule which is complementary to a given nucleotide sequence is one which is sufficiently complementary to the given nucleotide sequence that it can hybridize to the given nucleotide sequence thereby forming a stable duplex.

A nucleic acid molecule described herein can comprise only a portion of a nucleic acid sequence. Such nucleic acid molecules can be used, for example, as a probe or primer. The probe/primer can be one or more substantially purified oligonucleotides. Probes based on the sequence of a nucleic acid molecules described herein can be used to detect transcripts or genomic sequences corresponding to the genes described herein. The probe can contain comprise a label group, e.g., a radioisotope, a fluorescent compound, an enzyme, or an enzyme co-factor. Such probes can be used as part of a diagnostic test kit for identifying cells or tissues which express the protein, such as by measuring levels of a nucleic acid molecule encoding the protein in a sample of cells from a patient, e.g., detecting mRNA levels.

Methods for Detection of Gene Expression

Methods of detecting and/or quantifying a gene transcript, e.g., mRNA or cDNA made therefrom, can include but are not limited to Southern Blot analysis, Northern Blot analysis, polymerase chain reaction (PCR) analyses and probe arrays. Methods of detecting and/or quantifying a gene transcript, e.g., mRNA or cDNA made therefrom, can include but are not limited to hybridization based methods, e.g., hybridization with a probe that is specific for the gene transcript, e.g., mRNA or cDNA made therefrom. The level of a gene transcript, e.g., mRNA or cDNA made therefrom, can be assayed by applying the sample, or the mRNA or cDNA made therefrom, or amplified from; to a nucleic acid microarray, or chip array.

The level of a gene transcript, e.g., mRNA or cDNA made therefrom, can be assayed by a polymerase chain reaction (PCR) based method, e.g., quantitative PCR, quantitative real time PCR, real time PCR, reverse transcription PCR, real time reverse transcription PCR. The level of a gene transcript, e.g., mRNA or cDNA made therefrom, can be assayed by a sequencing based method, e.g., quantitative RNA sequencing.

The level of a gene transcript, e.g., mRNA, can be determined by in situ or by in vitro methods known in the art. For in vitro methods, any RNA isolation technique that does not select against the isolation of mRNA can be utilized for the purification of RNA from a sample, e.g., from cells of a sample (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155). For in situ methods, mRNA does not need to be isolated from the cells prior to detection. In such methods, a cell or tissue sample can be prepared/processed using known histological methods. The sample can then be immobilized on a support, and then contacted with a probe that can hybridize to mRNA that encodes the gene transcript of interest.

Determinations can be based on absolute expression level; normalized expression level, or relative expression level; of a gene transcript, e.g., mRNA. Expression levels can be normalized by correcting the absolute expression level of a gene transcript by comparing its expression level to the expression level of another gene which is stably expressed, e.g., a housekeeping gene that is constitutively expressed. Suitable genes for normalization include housekeeping genes such as histone H3 gene or the actin gene. This normalization allows the comparison of the expression level in one sample to another sample, e.g., a first sample taken from a patient to a second sample taken from the same patient, e.g., from another tissue or at a different time point; or between samples from different sources, e.g., a patient sample from one patient to a patient sample from another patient.

The expression level can be provided as a relative expression level. The relative expression level can be determined by comparing the absolute level of expression of the gene transcript, e.g., mRNA, to a reference standard. The reference standard can include the level of expression of the gene transcript of interest in a genotypically or phenotypically defined sample. The reference standard can be the level of expression of the gene transcript of interest, e.g., E-cadherin, vimentin, pyruvate carboxylase, in a cell genotypically or phenotypically characterized as an epithelial cell. An epithelial cell can be characterized as in any one of the following references: (Yauch et al., (2005) Clin Cancer Res 11:24; Savagner et al., (2010) Ann Oncol. 21(suppl 7): vii89; Thiery et al., (2002) Nature Reviews Cancer 2(6):442).

The expression level of a gene transcript described herein, e.g., E-cadherin, vimentin, pyruvate carboxylase, can be measured at least at two time-points to determine if a change in the level of expression has occurred. For example, the level of expression can be measured pre- and post-treatment with a therapeutic agent, e.g an inhibitor of glutamine-utilizing enzyme (e.g, glutaminase) or a glutamine-depleting agent or chemotherapeutic agent, or cancer treatment, or at one or more time-points while treatment with a therapeutic agent is ongoing. If the expression level is found to be decreased, e.g., decreased expression of E-cadherin compared to a reference standard and/or increased expression of vimentin compared to a reference standard; the subject may be administered treatment with an inhibitor of glutamine-utilizing enzyme (e.g, glutaminase) or a glutamine-depleting agent. The reference standard can be the level of expression of the gene transcript of interest in an epithelial cell characterized. An epithelial cell can be characterized by methods known in the art, e.g., as in any one of the following references: (Yauch et al., (2005) Clin Cancer Res 11:24; Savagner et al., (2010) Ann Oncol. 21(suppl 7): vii89; Thiery et al., (2002) Nature Reviews Cancer 2(6):442).

Proteins

The methods described herein can pertain to the evaluation of a sample for the expression of a gene described herein, e.g., E-cadherin, vimentin, pyruvate carboxylase; based on isolated proteins which correspond to the gene described herein, e.g., the protein level of E-cadherin; the protein level of vimentin; the protein level of pyruvate carboxylase. This can also include the evaluation of biologically active portions, variants, isoforms, or splice variants thereof. The native polypeptide corresponding to the protein of interest can be isolated from the sample by an appropriate purification scheme using standard protein purification techniques known to those of skill in the art.

An "isolated" or "purified" protein or biologically active portion thereof is substantially free of cellular material or other contaminating proteins from the cell or tissue source from which the protein is derived. The language "substantially free of cellular material" includes preparations of protein in which the protein is separated from cellular components of the cells from which it is isolated. Biologically active portions of a polypeptide can include polypeptides comprising amino acid sequences sufficiently identical to or derived from the amino acid sequence of the protein, which include fewer amino acids than the full length protein, and exhibit at least one activity of the corresponding full-length protein. Typically, biologically active portions comprise a domain or motif with at least one activity of the corresponding protein.

Methods for Detection of Protein Expression

The level of expression of a protein or polypeptide can be detected and quantified by any of a number of means well known to those of skill in the art. Methods of detecting and/or quantifying a protein or polypeptide described herein, e.g., E-cadherin, vimentin, pyruvate carboxylase; can include but are not limited to biochemical methods such as electrophoresis, capillary electrophoresis, high performance liquid chromatography (HPLC), thin layer chromatography (TLC), hyperdiffusion chromatography, and the like, or various immunoassays such as fluid or gel precipitin reactions, immunodiffusion (single or double), immunoelectrophoresis, radioimmunoassay (MA), enzyme-linked immunosorbent assays (ELISAs), immunofluorescent assays, Western blotting, immunohistochemistry, in situ hybridization, fluorescence-activated cell sorting (FACS) and the like. A skilled artisan can readily adapt known protein/antibody detection methods for use in determining whether cells express the protein or polypeptide described herein.

A protein or polypeptide can be detected using an immunoassay. As used herein, immunoassays include assays that utilizes an antibody to specifically bind to a protein or polypeptide. An immunoassay can be characterized by the detection of specific binding of a protein or polypeptide to an antibody as opposed to the use of other physical or chemical properties to isolate, target, and quantify the polypeptide. The polypeptide can be detected and/or quantified using any of a number of well recognized immunological binding assays (see, e.g., U.S. Pat. Nos. 4,366,241; 4,376, 110; 4,517,288; and 4,837,168). For a review of the general immunoassays, see also Asai (1993) *Methods in Cell Biology* Volume 37: *Antibodies in Cell Biology*, Academic Press, Inc. New York; Stites & Terr (1991) *Basic and Clinical Immunology* 7th Edition. Immunoassays for the detection and/or quantification of a protein or polypeptide can take a wide variety of formats well known to those of skill in the art.

An antibody capable of binding to a protein or polypeptide, e.g., an antibody with a detectable label (either directly or indirectly labeled), corresponding to a protein or polypeptide described herein, e.g., E-cadherin, vimentin, pyruvate carboxylase, can be used to detect the protein or polypeptide. Antibodies can be polyclonal or monoclonal. An intact antibody, or a fragment thereof, e.g., Fab or F(ab')$_2$ can be used. The term "labeled", with regard to the probe or antibody, is intended to encompass direct labeling of the probe or antibody by coupling, i.e., physically linking a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The antibody can also be labeled, e.g., a radio-labeled, chromophore-labeled, fluorophore-labeled, or enzyme-labeled antibody. An antibody derivative, e.g., an antibody conjugated with a substrate or with the protein or ligand of a protein-ligand pair, e.g., biotin-streptavidin, or an antibody fragment, e.g., a single-chain antibody, an isolated antibody hypervariable domain, etc, which binds specifically with a protein described herein, e.g., E-cadherin, vimentin, pyruvate carboxylase, such as the protein encoded by the open reading frame corresponding to the gene transcript of a protein or polypeptide described herein, e.g., E-cadherin, vimentin, pyruvate carboxylase, or such a protein or polypeptide which has undergone all or a portion of its normal post-translational modification, is used.

Proteins from cells can be isolated using techniques that are well known to those of skill in the art. The protein isolation methods employed can, for example, be such as those described in Harlow and Lane (Harlow and Lane, 1988, *Antibodies: A Laboratory Manual*, Cold Spring Harbor Laboratory Press, Cold Spring Harbor, N.Y.).

The expression level can be provided as a relative expression level. The relative expression level can be determined by comparing the absolute level of expression of the protein, to a reference standard. The reference standard can include the level of expression of the protein of interest in a genotypically or phenotypically defined sample. The reference standard can be the level of expression of the protein of interest, e.g., E-cadherin, vimentin, pyruvate carboxylase, in a cell genotypically or phenotypically characterized as an epithelial cell. An epithelial cell can be characterized by methods known in the art, e.g., as described in on any one of the following references: (Yauch et al., (2005) Clin Cancer Res 11:24; Savagner et al., (2010) Ann Oncol. 21(suppl 7): vii89; Thiery et al., (2002) Nature Reviews Cancer 2(6):442).

The expression level of a protein or polypeptide described herein, e.g., E-cadherin, vimentin, pyruvate carboxylase, can be measured at least at two time-points to determine if a change in the level of expression has occurred. For example, the level of expression can be measured pre- and post-treatment with a therapeutic agent, e.g., an inhibitor of glutamine-utilizing enzyme (e.g, glutaminase) or a glutamine-depleting agent or chemotherapeutic agent, or cancer treatment, or at one or more time-points while treatment with a therapeutic agent is ongoing. If the expression level is found to be decreased, e.g., decreased expression of E-cadherin compared to a reference standard and/or increased expression of vimentin compared to a reference standard; the subject may be administered treatment with a an inhibitor of glutamine-utilizing enzyme (e.g, glutaminase) or a glutamine-depleting agent.

Cancers

The methods described herein can be used with any cancer, for example those described by the National Cancer Institute. A cancer can be evaluated to determine whether it is using a method described herein. Exemplary cancers can include but are not limited to, lung cancer, e.g., non-small cell lung cancer; breast cancer; or hepatocellular carcinoma, osteosarcoma, lipomas, chondrosarcoma, or mesothelioma.

The cancer can be a primary tumor, i.e., located at the anatomical site of tumor growth initiation. The cancer can also be metastatic, i.e., appearing at least a second anatomical site other than the anatomical site of tumor growth initiation. The cancer can be a recurrent cancer, i.e., cancer that returns following treatment, and after a period of time in which the cancer was undetectable. The recurrent cancer can be anatomically located locally to the original tumor, e.g., anatomically near the original tumor; regionally to the original tumor, e.g., in a lymph node located near the original tumor; or distantly to the original tumor, e.g., anatomically in a region remote from the original tumor.

Inhibitor of a Glutamine-Utilizing Enzyme (e.g., Glutaminase) or a Glutamine-Depleting Agent The methods described herein can include methods of administering an inhibitor of glutamine-utilizing enzyme (e.g., glutaminase) or a glutamine-depleting agent for the treatment of cancer, such as lung cancer (e.g., non-small cell lung cancer), breast cancer, or hepatocellular carninoma.

GLS1 is a phosphate-activated amidohydrolase that catalyzes the hydrolysis of glutamine to glutamate and ammonia. The protein is highly expressed in the brain and kidney plays an essential role in generating energy for metabolism, synthesizing the brain neurotransmitter glutamate, and maintaining acid-base balance in the kidney. Alternate splicing results in multiple transcript variants, including canonical GLS1 (also known as KGA) and GAC. GLS1 is not consistently mutated or amplified in cancers. However, GLS1 gene expression can be upregulated during tumorigenesis.

GLS2 is a phosphate-activated glutaminase that catalyzes the hydrolysis of glutamine to stoichiometric amounts of glutamate and ammonia. GLS2 promotes mitochondrial respiration and increases ATP generation in cells by catalyzing the synthesis of glutamate and alpha-ketoglutarate. GLS2 also increases cellular anti-oxidant function via NADH and glutathione production.

The glutamine-depleting agent can include but is not limited to an asparaginase (such as Elspar® (Merck), Oncaspar® (Sigma Tau/Enzon), and Erwinaze® (EUSA)), a glutaminase including pegylated forms (such as those described in U.S. Pat. No. 7,052,689 and U.S. Pat. No. 6,312,939, content of each is incorporated herein by reference), or GlutaDon (as described in US2009/0169537, content of which is incorporated herein by reference).

The glutaminase (GLS) inhibitor can include but is not limited to bis-2-(5-phenylacetamido-1,2,4-thiadiazol-2-yl) ethyl sulfide (BPTES). In some embodiments, the GLS inhibitors are as described in U.S. Pat. No. 6,451,828; WO2010/111504 (US2012/0220610); WO2012/034123; WO2011/143160; U.S. Pat. No. 5,552,427 and WO2010/033871, the content of each is incorporated herein by reference. In some embodiments, the glutamine-utilizing enzyme inhibitor is as described in U.S. Pat. No. 7,714,007 (the content of which is incorporated herein by reference), such as an amidotransferase inhibitor, long chain fatty acid, 6-diazo-5-oxo-L-norleucine (DON), N-ethylmaleimide (NEM), p-chloromercuriphenylsulfonate (pCMPS), L-2-amino-4-oxo-5-chloropentoic acid, DON plus o-carbamoyl-L-serine, acivicin [(alphaS,5S)-alpha-amino-3-chloro-4,5-dihydro-5-isoxazoleacetic acid], azaserine, palmitoyl coenzyme A (CoA), stearoyl CoA, bromothymol blue, and dicoumarol.

A GLS inhibitor can include but is not limited to a small molecule GLS inhibitor, an antibody based GLS inhibitor; a nucleic acid based GLS inhibitor, e.g., a miRNA, shRNA, etc; or an agent which inhibits GLS interaction with other proteins. An exemplary GLS inhibitor is BPTES (bis-2-(5-phenylacetamido-1,2,4-thiadiazol-2-yl)ethyl sulfide).

Administration

The methods described herein can include methods of administering an inhibitor of a glutamine-utilizing enzyme (e.g., glutaminase) or a glutamine-depleting agent for the treatment of cancer. An exemplary an inhibitor of glutamine-utilizing enzyme (e.g., glutaminase) is BPTES (bis-2-(5- phenylacetamido-1,2,4-thiadiazol-2-yl)ethyl sulfide). The methods described herein can further include selecting a regimen, e.g., dosage, formulation, route of administration, number of dosages, or adjunctive or combination therapies of the GLS inhibitor. The administration of the inhibitor of a glutamine-utilizing enzyme (e.g., glutaminase) or the glutamine-depleting agent can be responsive to the acquisition of an evaluation of the level of expression of a gene described herein, e.g., E-cadherin, vimentin, pyruvate carboxylase, and/or classification of a patient as a candidate or non-candidate for treatment with an inhibitor of a glutamine-utilizing enzyme (e.g., glutaminase) or a glutamine-depleting agent. The methods described herein can further include the administration of the selected regimen. The administration can be provided responsive to acquiring knowledge or information of an evaluation of the level of expression of a gene described herein, e.g., E-cadherin, vimentin, pyruvate carboxylase, from another party; or receiving communication of an evaluation of the level of expression of a gene described herein, e.g., E-cadherin, vimentin, pyruvate carboxylase, wherein the acquisition arises from collaboration with another party.

The inhibitor of a glutamine-utilizing enzyme (e.g., glutaminase) or the glutamine-depleting agent can be administered to a patient using any effective amount and any route of administration effective. The exact dosage required will vary from patient to patient, depending on patient specific factors, e.g., the age and general condition of the patient, concurrent treatments, concurrent diseases or conditions; cancer specific factors, e.g., the type of cancer, whether the cancer is recurrent, whether the cancer is metastatic, the severity of the disease; and agent specific factors, e.g., its composition, its mode of administration, its mode of activity, and the like. For example, the dosage may vary depending on whether the patient is currently receiving or had previously received a treatment regimen prior to the administration of a cancer treatment; whether the patient is a non-responder to such current or previous treatment; whether the patient's cancer is recurrent; or whether the patient's cancer has metastasized to a second tissue site.

The total daily usage of a cancer treatment can be decided by an attending physician within the scope of sound medical judgment. The specific therapeutically effective, dose level for any particular patient will depend upon a variety of factors including the type of cancer being treated; the severity of the cancer; the metastatic state of the cancer; the recurrence state of the cancer; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The cancer treatment may be administered by any route, including by those routes currently accepted and approved for known products. Exemplary routes of administration include, e.g., oral, intraventricular, transdermal, rectal, intravaginal, topical (e.g. by powders, ointments, creams, gels, lotions, and/or drops), mucosal, nasal, buccal, enteral, vitreal, sublingual; by intratracheal instillation, bronchial instillation, and/or inhalation; as an oral spray, nasal spray, and/or aerosol, and/or through a portal vein catheter. An agent may be administered in a way, which allows the agent to cross the blood-brain barrier, vascular barrier, or other epithelial barrier. Other exemplary routes include administration by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular, intraarterial, intrathecal, intracapsular, intramedullary, intratumoral, intraorbital, intracardiac, intradermal, intraperitoneal, transtracheal, subcutaneous, subcuticular, intraarticular, subcapsular, subarachnoid, intraspinal, epidural and intrasternal injection and infusion.

Pharmaceutical compositions can be formulated in a variety of different forms, such as liquid, semi-solid and solid dosage forms, such as liquid solutions (e.g., injectable and infusible solutions), dispersions or suspensions, tablets, pills, powders, liposomes and suppositories. The preferred form can depend on the intended mode of administration and therapeutic application. A pharmaceutical composition comprising an agent that inhibits or kills cancer associated mesenchymal cells, tumor initiating cancer cells, or cancer stem cells may be administered on various dosing schedules. The dosing schedule will be dependent on several factors including, the type of cancer being treated; the severity of the cancer; the metastatic state of the cancer; the recurrence state of the cancer; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Exemplary dosing schedules can include, once daily, or once weekly, or once monthly, or once every other month. The composition can be administered twice per week or twice per month, or once every two, three or four weeks. The composition can be administered as two, three, or more sub-doses at appropriate intervals throughout the day or even using continuous infusion or delivery through a controlled release formulation. In that case, the therapeutic agent contained in each sub-dose may be correspondingly smaller in order to achieve the total daily dosage. The dosage can also be compounded for delivery over several days, e.g., using a conventional sustained release formulation, which provides sustained release of the agent over a several day period. Sustained release formulations are well known in the art and are particularly useful for delivery of agents at a particular site.

Combination Therapy

The inhibitor of a glutamine-utilizing enzyme (e.g., glutaminase) or the glutamine-depleting agent, can be used in combination with an additional therapeutic agent. By "in combination with," it is not intended to imply that the inhibitor of glutamine-utilizing enzyme (e.g, glutaminase) or the glutamine-depleting agent and additional therapeutic agent must be administered at the same time and/or formulated for delivery together, although these methods of delivery are certainly within the scope of the methods described herein. The inhibitor of a glutamine-utilizing enzyme (e.g., glutaminase) or the glutamine-depleting agent can be administered concurrently, prior to or subsequent to, one or more additional therapeutic agents. In general, the inhibitor of a glutamine-utilizing enzyme (e.g., glutaminase) or the glutamine-depleting agent and the therapeutic agent will be administered at a dose and/or on a time schedule determined for each. It will further be appreciated that the inhibitor of a glutamine-utilizing enzyme (e.g., glutaminase) or the glutamine-depleting agent and the additional therapeutic agent utilized in this combination can be administered together in a single pharmaceutical composition or administered separately in different pharmaceutical compositions. The particular combination to employ in a regimen will take into account compatibility of the cancer treatment with the additional therapeutic agent and/or the desired therapeutic effect to be achieved.

The inhibitor of a glutamine-utilizing enzyme (e.g., glutaminase) or the glutamine-depleting agent and the additional therapeutic agent can be administered concurrently. For example, the inhibitor of a glutamine-utilizing enzyme (e.g., glutaminase) or the glutamine-depleting agent and the additional therapeutic agent are administered at the same time; on the same day; or within the same treatment regimen. The inhibitor of a glutamine-utilizing enzyme (e.g., glutaminase) or the glutamine-depleting agent can be administered before the additional therapeutic agent on the same day or within the same treatment regimen. The inhibitor of a glutamine-utilizing enzyme (e.g., glutaminase) or the glutamine-depleting agent can be concurrently administered with additional therapeutic agent for a period of time, after which point treatment with the additional therapeutic agent is stopped and treatment with the cancer treatment continues. The inhibitor of a glutamine-utilizing enzyme (e.g., glutaminase) or the glutamine-depleting agent can be administered concurrently with the additional therapeutic agent for a period of time, after which the inhibitor of a glutamine-utilizing enzyme (e.g., glutaminase) or the glutamine-depleting agent treatment is stopped and treatment with the additional therapeutic agent continues. The inhibitor of a glutamine-utilizing enzyme (e.g., glutaminase) or the glutamine-depleting agent and the additional therapeutic agent can be administered sequentially. For example, the inhibitor of a glutamine-utilizing enzyme (e.g., glutaminase) or the glutamine-depleting agent is administered after the treatment regimen of the additional therapeutic agent has ceased; or the additional therapeutic agent can be administered after the treatment regimen of the inhibitor of a glutamine-utilizing enzyme (e.g., glutaminase) or the glutamine-depleting agent has ceased.

The inhibitor of a glutamine-utilizing enzyme (e.g., glutaminase) or the glutamine-depleting agent can be a first line treatment for the cancer, i.e., it is used in a patient who has not been previously administered another drug intended to treat the cancer; a second line treatment for the cancer, i.e., it is used in a patient who has been previously administered another drug intended to treat the cancer; a third or fourth line treatment for the cancer, i.e., it is used in a patient who has been previously administered two or three other drugs intended to treat the cancer.

Additional Therapeutic Agents

Exemplary additional therapeutic agents can include, but are not limited to chemotherapeutic agents, e.g., epidermal growth factor receptor (EGFR) inhibitors, e.g., cetuximab, panitumumab, gefitinib, erlotinib, nimotuzamab, matuzamab, zalutumumab, or lapatinib. Resistance to EGFR inhibitors can occur as a result of the transition of a cell to a mesenchymal phenotype or a mesenchymal phenotype, and tumors with EGFR mutations and mesenchymal phenotype can be less sensitive to EGFR inhibitors (see for example, Sequist et al., (2011) Sci Transl Med. 3:75. Buck et al., (2007) Mol Cancer Ther. 6: 532; Thomson et al., (2008) Clin Exp Metastasis 25: 843).

Kits and Products

Also described herein are kits and products comprising a means to assay the level of gene expression of a gene described herein, e.g., E-cadherin, vimentin, pyruvate carboxylase. For example, the kit or product can include an agent capable of interacting with a gene expression product of a gene described herein, e.g., E-cadherin, vimentin, pyruvate carboxylase. The kit or product can include a plurality of agents capable of interacting with gene expression products of a plurality of genes described herein, e.g., E-cadherin, vimentin, pyruvate carboxylase. The agent can include, but is not limited to, an antibody, a plurality of antibodies, an oligonucleotide, or a plurality of oligonucleotides. The gene expression product can include, but is not limited to, a transcribed molecule, a RNA molecule, a polypeptide, a protein, genomic DNA, or cDNA.

The kit or product can further optionally include reagents for performing the assays described herein. For example, the kit can include buffers, solvents, stabilizers, preservatives, purification columns, detection reagents, and enzymes, which may be necessary for isolating nucleic acids from a patient sample, amplifying the samples, e.g., by qRT-PCR, and applying the samples to the agent described above; or for isolating proteins from a subject sample, and applying the samples to the agent described above; or reagents for directly applying the subject sample to the agent described above. A kit can also include positive and negative control samples, e.g., control nucleic acid samples (e.g., nucleic acid sample from a non-cancer subject, or a non-tumor tissue sample, or a subject who has not received treatment for cancer, or other test samples for testing at the same time as subject samples. A kit can also include instructional material, which may provide guidance for collecting and processing patient samples, applying the samples to the level of gene expression assay, and for interpreting assay results.

The components of the kit can be provided in any form, e.g., liquid, dried, semi-dried, or in lyophilized form, or in a form for storage in a frozen condition. Typically, the components of the kit are provided in a form that is sterile. When reagents are provided in a liquid solution, the liquid solution generally is an aqueous solution, e.g., a sterile aqueous solution. When reagents are provided in a dried form, reconstitution generally is accomplished by the addition of a suitable solvent. The solvent, e.g., sterile buffer, can optionally be provided in the kit.

The kit can include one or more containers for the kit components in a concentration suitable for use in the level of gene expression assays or with instructions for dilution for use in the assay. The kit can contain separate containers, dividers or compartments for the assay components, and the informational material. For example, the positive and negative control samples can be contained in a bottle or vial, the clinically compatible classifier can be sealed in a sterile plastic wrapping, and the informational material can be contained in a plastic sleeve or packet. The kit can include a plurality (e.g., a pack) of individual containers, each containing one or more unit forms (e.g., for use with one assay) of an agent. The containers of the kits can be air tight and/or waterproof. The container can be labeled for use.

The kit can include informational material for performing and interpreting the assay. The kit can also provide guidance as to where to report the results of the assay, e.g., to a treatment center or healthcare provider. The kit can include forms for reporting the results of a gene activity assay described herein, and address and contact information regarding where to send such forms or other related information; or a URL (Uniform Resource Locator) address for reporting the results in an online database or an online application (e.g., an app). In another embodiment, the informational material can include guidance regarding whether a patient should receive treatment with an ant-cancer stem cell agent, depending on the results of the assay.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as computer readable material, video recording, or audio recording. The informational material of the kit can be contact information, e.g., a physical address, email address, website, or telephone number, where a user of the kit can obtain substantive information about the gene activity assay and/or its use in the methods described herein. The informational material can also be provided in any combination of formats.

A subject sample can be provided to an assay provider, e.g., a service provider (such as a third party facility) or a healthcare provider that evaluates the sample in an assay and provides a read out. For example, an assay provider can receive a sample from a subject, such as a tissue sample, or a plasma, blood or serum sample, and evaluate the sample using an assay described herein, and determines that the subject is a candidate to receive treatment with an inhibitor of a glutamine-utilizing enzyme (e.g., glutaminase) or a glutamine-depleting agent. The assay provider can inform a healthcare provider that the subject is a candidate for treatment with an inhibitor of a glutamine-utilizing enzyme (e.g., glutaminase) or a glutamine-depleting agent, and the candidate is administered the inhibitor of a glutamine-utilizing enzyme (e.g., glutaminase) or the glutamine-depleting agent. The assay provider can provide the results of the evaluation, and optionally, conclusions regarding one or more of diagnosis, prognosis, or appropriate therapy options to, for example, a healthcare provider, or patient, or an insurance company, in any suitable format, such as by mail or electronically, or through an online database. The information collected and provided by the assay provider can be stored in a database.

EXAMPLES

Figure 3A:
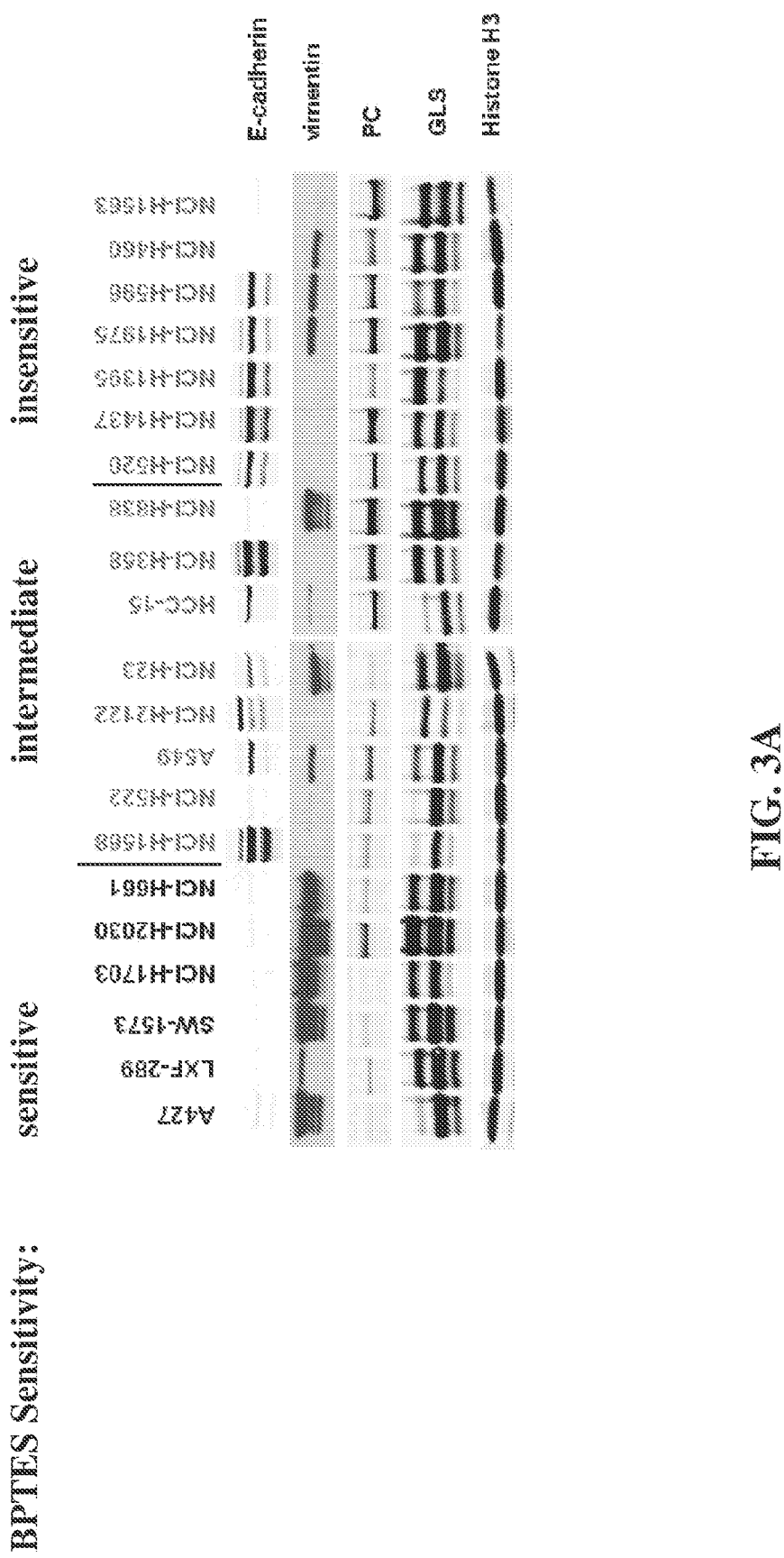
FIG. 3A depicts a western blot analysis of 20 non-small cell lung cancer cell lines for protein levels of E-cadherin, vimentin, PC (pyruvate decarboxylase), GLS (phosphate activated glutaminase), and histone 3 (control). The sensitivity of each cell line to BPTES is indicated as sensitive, intermediate, or insensitive.
Figure 3B:
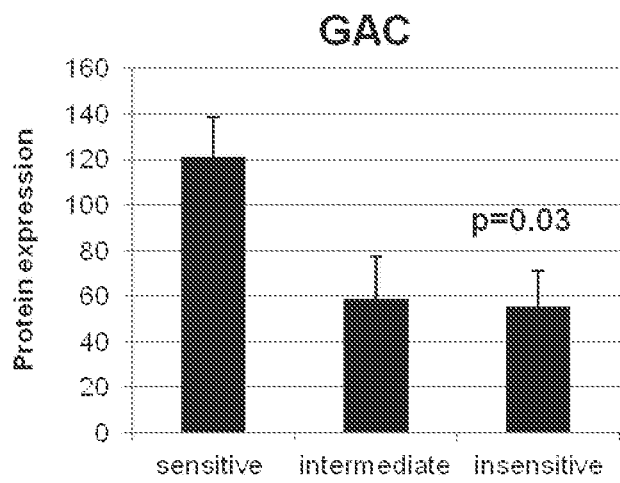
FIG. 3B depicts GAC and FIG. 3C depicts PC (pyruvate decarboxylase) protein expression in non-small cell lung cancer cell lines which are characterized as sensitive, intermediate, or insensitive to BPTES.
Figure 3C:
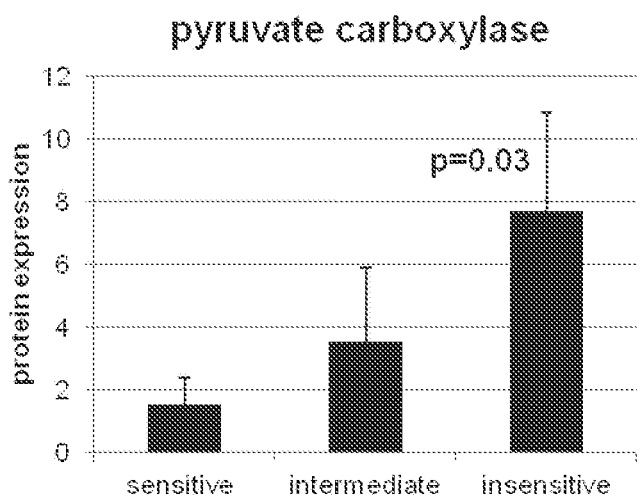

Example 1. E-Cadherin and Vimentin are Negatively and Positively, Respectively, Correlated with BPTES Sensitivity in Lung Cancer Cell Lines A panel of 62 lung cancer cell lines were screened for sensitivity to the GLS inhibitor BPTES (bis-2-(5-phenylacetamido-1,2,4-thiadiazol-2-yl)ethyl sulfide) (Table 1). Of these, 44 of the cell lines have been classified as non-small cell lung cancer (NSCLC). Approximately 30% of the 62 lines exhibited significant sensitivity to BPTES ($\mu/\mu_{max}$<0.6). FIG. 1 shows growth response curves of three NSCLC cell lines (LXF-289; NCI-H1703; NCI-H460) to BPTES. As exemplified in FIG. 1, there were qualitative differences in sensitivity of these cell lines to BPTES. Over the course of the 72 hr proliferation assay some cell lines exhibited predominantly cytostatic effects in response to BPTES, e.g., NCI-H1703, while others exhibited cell death, e.g., LXF289. Using the BPTES sensitivity data in Table 1, transcriptional markers associated BPTES sensitivity or resistance were searched for using publicly available datasets. The top 200 probes showed the most significant correlation with $\mu/\mu_{max}$ submitted to GeneGO pathway analysis (FIG. 2). No metabolism-related pathways were strongly associated with BPTES responsiveness, indicating that any intrinsic differences in metabolism between BPTES sensitive and BPTES resistant cells is not broadly reflected at the transcriptional level. Four of the top 25 transcriptional/cellular pathways were related to the epithelial-mesenchymal transition (EMT) (ranks 1, 15, 23, 25 of FIG. 2). RNA expression from this analysis indicated that E-cadherin and vimentin were negatively and positively correlated with sensitivity, respectively. Western blot analysis from a subset of 20 of the NSCLC cell lines indicated that there was a corroborating pattern of protein levels for these transcriptional profiling markers (FIG. 3A). In the 7 most sensitive NSCLC cell lines, without exception, low E-cadherin and high vimentin protein levels were observed (FIG. 3B). Low E-cadherin/high vimentin are well-defined markers of cells that have a mesenchymal phenotype as characterized for example, in any one of the following references: (Yauch et al., (2005) Cin Cancer Res 11:24; Savagner et al., (2010) Ann Oncol. 21(suppl 7): vii89; Thiery et al., (2002) Nature Reviews Cancer June vol 2:442).

TABLE 1

Panel of 62 lung cancer cell lines screened for sensitivity to the GLS inhibitor BPTES.

| Cell Line | μ/μmax | Tissue: Cancer Classification |
| --- | --- | --- |
| A427 | −0.49 | Lung: Non-small cell lung cancer |
| LXF-289 | −0.25 | Lung: Non-small cell lung cancer |
| NCI-H1734 | −0.12 | Lung: Non-small cell lung cancer |
| SW-1573 | 0.12 | Lung: Non-small cell lung cancer |
| NCI-H1568 | 0.25 | Lung: Non-small cell lung cancer |
| NCI-H1650 | 0.26 | Lung: Non-small cell lung cancer |
| NCI-H1703 | 0.30 | Lung: Non-small cell lung cancer |
| NCI-H2030 | 0.37 | Lung: Non-small cell lung cancer |
| NCI-H661 | 0.43 | Lung: Non-small cell lung cancer |
| NCI-H1299 | 0.49 | Lung: Non-small cell lung cancer |
| NCI-H1581 | 0.51 | Lung: Non-small cell lung cancer |
| NCI-H1618 | 0.53 | Lung |
| NCI-H524 | 0.53 | Lung: Non-small cell lung cancer |
| A549 | 0.53 | Lung: Non-small cell lung cancer |
| NCI-H774 | 0.54 | Lung |
| NCI-H1770 | 0.56 | Lung: Non-small cell lung cancer |
| NCI-H2122 | 0.56 | Lung: Non-small cell lung cancer |
| DMS-153 | 0.58 | Lung |
| NCI-H23 | 0.60 | Lung: Non-small cell lung cancer |
| NCI-H1395 | 0.61 | Lung: Non-small cell lung cancer |
| NCI-H522 | 0.61 | Lung |
| NCI-H1838 | 0.63 | Lung: Non-small cell lung cancer |
| HCC15 | 0.64 | Lung: Non-small cell lung cancer |
| NCI-H209 | 0.64 | Lung |
| NCI-H838 | 0.66 | Lung: Non-small cell lung cancer |
| NCI-H358 | 0.66 | Lung: Non-small cell lung cancer |
| NCI-H1436 | 0.68 | Lung |
| H2228 | 0.69 | Lung: Non-small cell lung cancer |
| SW900 | 0.70 | Lung: Non-small cell lung cancer |
| NCI-H1975 | 0.75 | Lung: Non-small cell lung cancer |
| NCI-H748 | 0.76 | Lung |
| NCI-H1092 | 0.77 | Lung |
| NCI-H1355 | 0.78 | Lung: Non-small cell lung cancer |
| NCI-H1373 | 0.79 | Lung: Non-small cell lung cancer |
| NCI-H2107 | 0.79 | Lung |
| NCI-H520 | 0.79 | Lung: Non-small cell lung cancer |
| NCI-H1623 | 0.79 | Lung: Non-small cell lung cancer |
| NCI-H1437 | 0.81 | Lung: Non-small cell lung cancer |
| CALU-6 | 0.82 | Lung: Non-small cell lung cancer |
| NCI-H2170 | 0.82 | Lung: Non-small cell lung cancer |
| NCI-H446 | 0.84 | Lung |
| NCI-H596 | 0.84 | Lung: Non-small cell lung cancer |
| COR-L279 | 0.88 | Lung |
| NCI-H2171 | 0.88 | Lung |
| NCI-H1993 | 0.89 | Lung: Non-small cell lung cancer |
| NCI-H292 | 0.89 | Lung |
| NCI-H82 | 0.90 | Lung |
| NCI-H2347 | 0.90 | Lung: Non-small cell lung cancer |
| NCI-H2405 | 0.92 | Lung: Non-small cell lung cancer |
| NCI-H1573 | 0.92 | Lung: Non-small cell lung cancer |
| NCI-H460 | 0.92 | Lung: Non-small cell lung cancer |
| NCI-H1563 | 0.92 | Lung: Non-small cell lung cancer |

TABLE 1-continued

Panel of 62 lung cancer cell lines screened for sensitivity to the GLS inhibitor BPTES.

| Cell Line | μ/μmax | Tissue: Cancer Classification |
|---|---|---|
| DMS-53 | 0.93 | Lung |
| NCI-H1155 | 0.93 | Lung: Non-small cell lung cancer |
| NCI-H1048 | 0.94 | Lung |
| COR-L23 | 0.96 | Lung: Non-small cell lung cancer |
| NCI-H2009 | 0.96 | Lung: Non-small cell lung cancer |
| NCI-H2126 | 1.00 | Lung: Non-small cell lung cancer |
| NCI-H2081 | 1.00 | Lung |
| NCI-H1651 | 1.00 | Lung: Non-small cell lung cancer |
| NCI-H1694 | 1.00 | Lung |
| NCI-H1666 | 1.00 | Lung: Non-small cell lung cancer |

Two exceptions to the correlation between the mesenchymal phenotype and sensitivity to GLS inhibition were the NCI-H838 and NCI-H460 cell lines (FIG. 3A). NCI-H838 cells exhibit only a moderate level of sensitivity to BPTES in spite of expressing low E-cadherin/high vimentin (Table 2, FIG. 3A); however these cells also express high levels of pyruvate carboxylase (PC) (FIG. 3A). Dependence of glioma and hepatocellular cancer cells on glutamine has been shown to be modulated by the expression of pyruvate carboxylase since this enzyme allows entry of carbon into the TCA via a glutamine (Gln) independent mechanism. Although not without exception, low pyruvate carboxylase protein levels also correlated well with sensitivity to BPTES in the panel of cell lines examined (FIGS. 3A, B and C), suggesting that alternative modes of carbon entry into the TCA could potentially modulate GLS dependence.

TABLE 2

NSCLC cell line sensitivity to BPTES and cell line genetic mutations.

| Cell Line | Tissue: Cancer Classification | μ/μmax @10 uM | Mutation Status (COSMIC) |
|---|---|---|---|
| A427 | Lung: Non-small cell lung cancer | −0.49 | CDKN2A, CDKN2a.p14., CTNNB1, KRAS, SMARCA4, STK11 |
| A549 | Lung: Non-small cell lung cancer | 0.53 | CDKN2A, CDKN2a.p14., KRAS, SMARCA4, STK11 |
| HCC15 | Lung: Non-small cell lung cancer | 0.64 | |
| LXF-289 | Lung: Non-small cell lung cancer | −0.25 | CDKN2A, CTNNB1, TP53 |
| NCI-H1395 | Lung: Non-small cell lung cancer | 0.61 | BRAF, FLCN, STK11 |
| NCI-H1437 | Lung: Non-small cell lung cancer | 0.81 | CDKN2A, CDKN2a.p14., TP53 |
| NCI-H1563 | Lung: Non-small cell lung cancer | 0.92 | CDKN2A, CDKN2a.p14., STK11 |
| NCI-H1568 | Lung: Non-small cell lung cancer | 0.25 | |
| NCI-H1703 | Lung: Non-small cell lung cancer | 0.30 | CDKN2A, TP53 |
| NCI-H1975 | Lung: Non-small cell lung cancer | 0.75 | CDKN2A, EGFR, PIK3CA, TP53 |
| NCI-H2030 | Lung: Non-small cell lung cancer | 0.37 | KRAS, SMARCA4, STK11, TP53 |
| NCI-H2122 | Lung: Non-small cell lung cancer | 0.56 | CDH1, CDKN2A, CDKN2a.p14., KRAS, STK11, TP53 |
| NCI-H23 | Lung: Non-small cell lung cancer | 0.60 | FGFR2, KRAS, SMARCA4, STK11, TP53 |
| NCI-H358 | Lung: Non-small cell lung cancer | 0.66 | KRAS |
| NCI-H460 | Lung: Non-small cell lung cancer | 0.92 | CDKN2A, CDKN2a.p14., KRAS, PIK3CA, STK11 |
| NCI-H520 | Lung: Non-small cell lung cancer | 0.79 | CDKN2A, TP53 |
| NCI-H522 | Lung: Non-small cell lung cancer | 0.61 | TP53 |
| NCI-H596 | Lung: Non-small cell lung cancer | 0.84 | PIK3CA, RB1, TP53 |
| NCI-H661 | Lung: Non-small cell lung cancer | 0.43 | CDKN2A, SMARCA4, TP53 |
| NCI-H838 | Lung: Non-small cell lung cancer | 0.66 | CDKN2A, CDKN2a.p14., SMARCA4, STK11, TP53 |
| SW-1573 | Lung: Non-small cell lung cancer | 0.12 | CDKN2A, CDKN2a.p14., CTNNB1, KRAS, NF2, PIK3CA, SMAD4 |

The three NSCLC lines that were most sensitive to BPTES (A427, LXF289, SW1573) all carry activating mutations in β-catenin (T41A in A427 and LXF289, T33F in A427, Table 3). Wnt/β-catenin signaling is one of several pathways that have been implicated in driving EMT. As a result, siRNA mediated knockdown of β-catenin in A427 cells were used to determine if loss of mutated β-catenin resulted in a change in sensitivity to BPTES.

TABLE 3

Cell lines and corresponding mutational status

| Cell Line | Tissue | Max Inh @ 10 uM (%) | Mu/max @10 uM | Mutation Status (COSMIC) |
|---|---|---|---|---|
| LXF-289 | lung: nsclc | 91 | −0.25 | CDKN2A, CTNNB1, TP53 |
| NCI-H1703 | lung: nsclc | 87 | 0.30 | CDKN2A, TP53 |
| NCI-H2030 | lung: nsclc | 87 | 0.37 | KRAS, SMARCA4, STK11, TP53 |
| A427 | lung: nsclc | 86 | −0.49 | CDKN2A, CDKN2a.p14., CTNNB1, KRAS, SMARCA4, STK11 |

TABLE 3-continued

Cell lines and corresponding mutational status

| Cell Line | Tissue | Max Inh @ 10 uM (%) | Mu/max @10 uM | Mutation Status (COSMIC) |
|---|---|---|---|---|
| A549 | lung: nsclc | 73 | 0.53 | CDKN2A, CDKN2a.p14., KRAS, SMARCA4, STK11 |
| NCI-H661 | lung: nsclc | 73 | 0.43 | CDKN2A, SMARCA4, TP53 |
| SW-1573 | lung: nsclc | 68 | 0.12 | CDKN2A, CDKN2a.p14., CTNNB1, KRAS, NF2, PIK3CA, SMAD4 |
| NCI-H2122 | lung: nsclc | 58 | 0.56 | CDH1, CDKN2A, CDKN2a.p14., KRAS, STK11, TP53 |
| NCI-H1568 | lung: nsclc | 50 | 0.25 | |
| NCI-H23 | lung: nsclc | 45 | 0.60 | FGFR2, KRAS, SMARCA4, STK11, TP53 |
| HCC15 | lung: nsclc | 40 | 0.64 | |
| NCI-H522 | lung: nsclc | 39 | 0.61 | TP53 |
| NCI-H838 | lung: nsclc | 37 | 0.66 | CDKN2A, CDKN2a.p14., SMARCA4, STK11, TP53 |
| NCI-H1437 | lung: nsclc | 27 | 0.81 | CDKN2A, CDKN2a.p14., TP53 |
| NCI-H358 | lung: nsclc | 27 | 0.66 | KRAS |
| NCI-H1975 | lung: nsclc | 18 | 0.75 | CDKN2A, EGFR, PIK3CA, TP53 |
| NCI-H460 | lung: nsclc | 18 | 0.92 | CDKN2A, CDKN2a.p14., KRAS, PIK3CA, STK11 |
| NCI-H1395 | lung: nsclc | 16 | 0.61 | BRAF, FLCN, STK11 |
| NCI-H520 | lung: nsclc | 14 | 0.79 | CDKN2A, TP53 |
| NCI-H596 | lung: nsclc | 13 | 0.84 | PIK3CA, RB1, TP53 |
| NCI-H1563 | lung: nsclc | 8 | 0.92 | CDKN2A, CDKN2a.p14., STK11 |

Figure 4A:
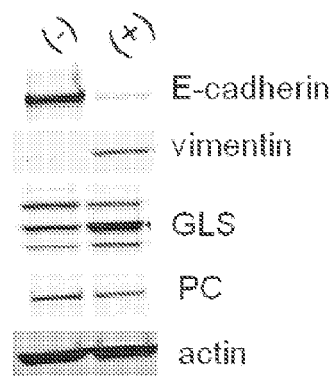
FIG. 4A depicts a western blot analysis of the non-small cell lung cancer cell line NCI-H358 for protein levels of E-cadherin, vimentin, PC (pyruvate decarboxylase), GLS (phosphate activated glutaminase), and actin (control).
Figure 4B:
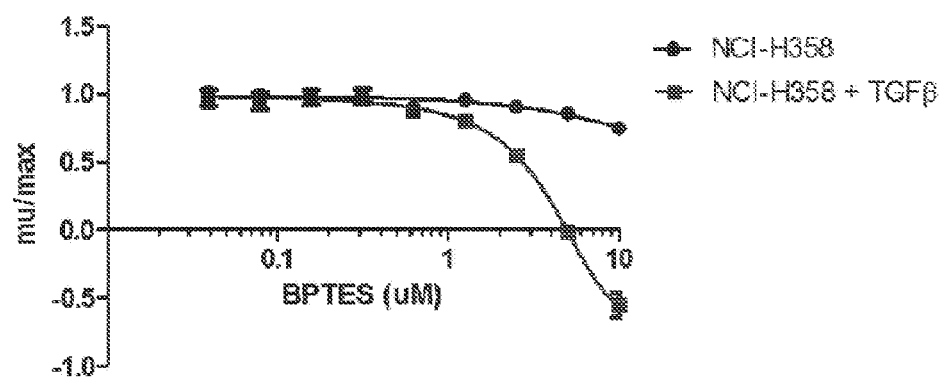
FIG. 4B depicts the growth response curves of the non-small cell lung cancer cell line NCI-H358 treated with varying concentrations of the GLS inhibitor BPTES, and cultured in the presence or absence of TGFβ.

In order to better understand the contribution of mesenchymal versus epithelial phenotype to GLS dependence, the NCI-H358 cell line was treated with TGFβ and the phenotype assayed. The NCI-H358 cell line is phenotypically epithelial (high E-cadherin/low vimentin expression, FIGS. 3A, B and C), is relatively BPTES insensitive (FIG. 2), and have been shown to undergo EMT in response to treatment with TGFβ. Treatment of the NCI-H358 line resulted in a shift to a mesenchymal phenotype with low E-cadherin/high vimentin expression (FIG. 4A). Notably, in addition to alterations in E-cadherin/vimentin expression with TGFβ induced EMT, GAC levels were also altered with this treatment, with a 2-fold increase in protein levels in the mesenchymal variant (FIG. 3A). Across the panel of 21 NSCLC cell lines examined, GAC levels were similarly found to be elevated by 2-fold (p=0.03) across the group of BPTES sensitive compared to insensitive lines (FIGS. 3A and 3B).

Figures 5A, 5B, 5C, 5D, 5E, 5F, 5G:
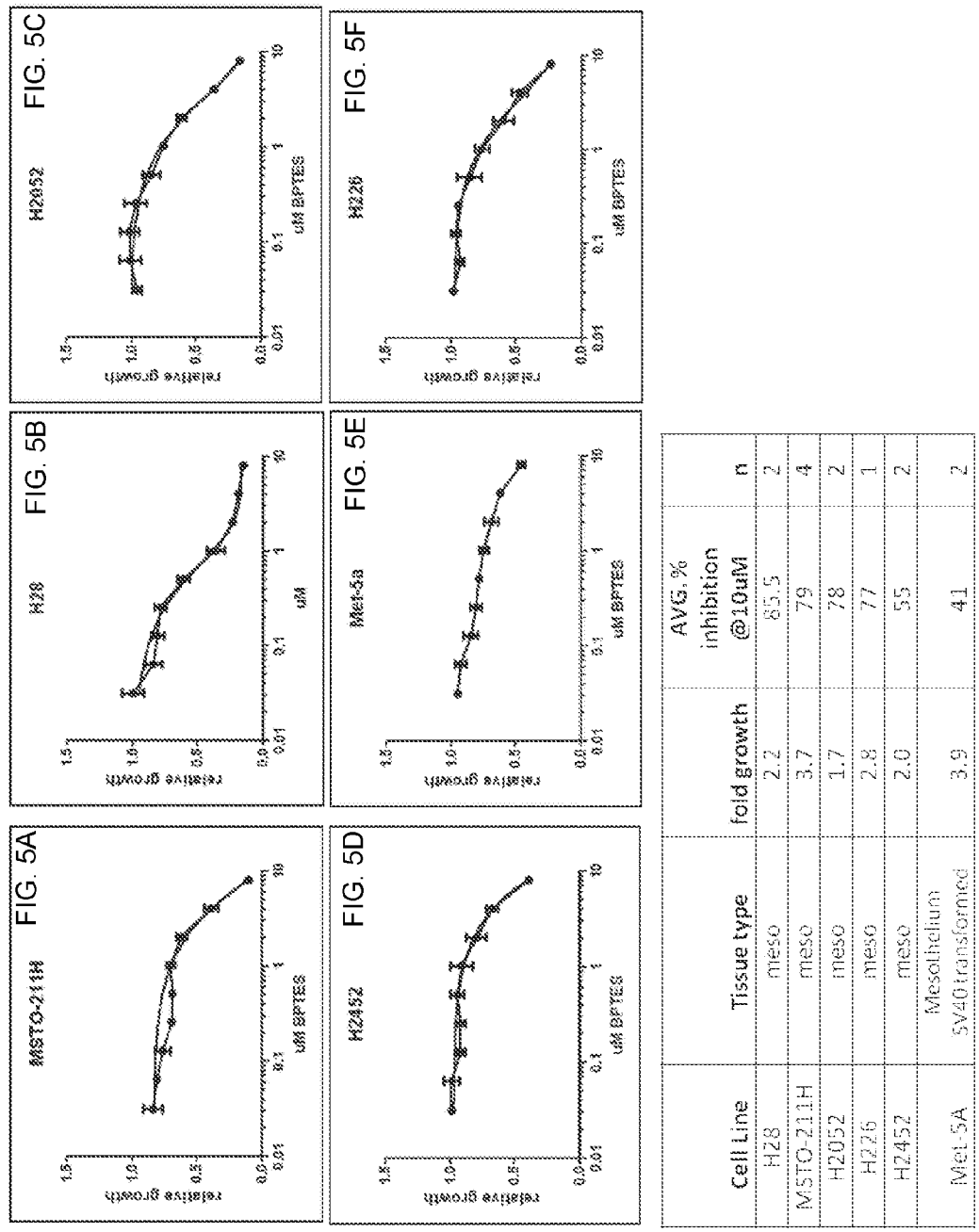
FIGS. 5A, 5B, 5C, 5D, and 5F depict the growth response curves of five mesothelioma cancer cell lines (MSTO-21H, H28, H2052, H2452, and H226, respectively) treated with varying concentrations of the GLS inhibitor BPTES.
FIG. 5E depicts the Met-5A cell line, a normal mesothelioma cell line.
FIG. 5G depicts the fold growth and average percent growth inhibition of five mesothelioma cancer cell lines (H28; MSTO-211H; H2052; H226; H2452) treated with 10 μM of the GLS inhibitor BPTES. The Met-5A cell line is a normal mesothelioma cell line.
Figure 5H:
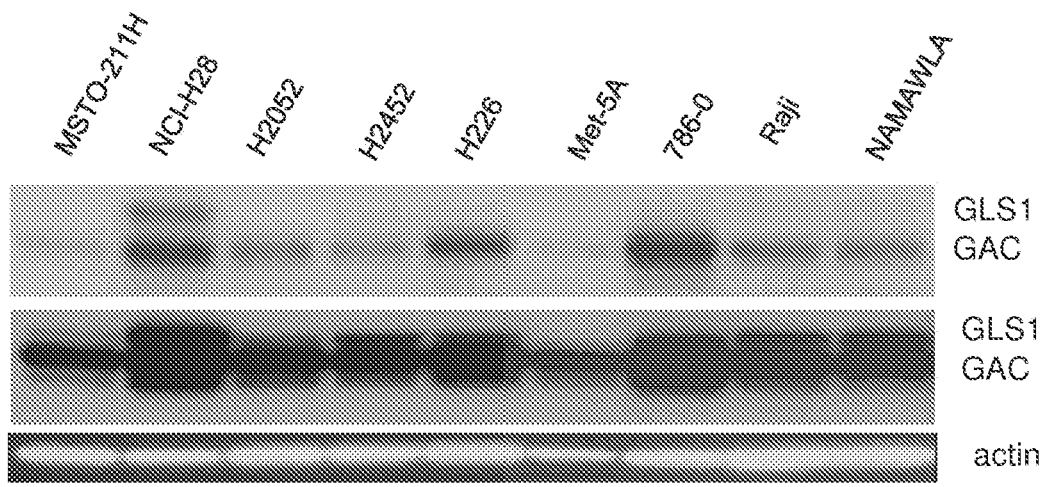
FIG. 5H depicts a western blot analysis of mesothelioma cancer cell lines for protein levels of GLS1 (phosphate activated glutaminase 1), GAC, and actin (control); in the absence of the GLS inhibitor BPTES (upper panel of the figure is the protein signal after a short developing exposure time and the middle panel is the protein signal after a long developing exposure time). The Met-5A cell line is a normal mesothelioma cell line.

Example 2. E-Cadherin and Vimentin are Negatively and Positively, Respectively, Correlated with BPTES Sensitivity in Mesothelioma Cancer Cell Lines A panel of five mesothelioma cancer cell lines were screened for sensitivity to the GLS inhibitor BPTES (bis-2-(5-phenylacetamido-1,2,4-thiadiazol-2-yl)ethyl sulfide) (FIGS. 5A-5H). FIG. 5A shows growth response curves of five mesothelioma cancer cell lines (H28; MSTO-211H; H2052; H226; H2452) treated with varying concentrations of the GLS inhibitor BPTES. The MET-5A cell line is a normal mesothelioma cell line. FIG. 5B shows the fold growth and average percent growth inhibition of five mesothelioma cancer cell lines (H28; MSTO-211H; H2052; H226; H2452) treated with 10 μM of the GLS inhibitor BPTES. FIG. 5C depicts a western blot analysis of mesothelioma cancer cell lines for protein levels of GLS (phosphate activated glutaminase 1), GAC, and actin (control); in absence of the GLS inhibitor BPTES (upper panel of the figure is the protein signal after a short developing exposure time and the middle panel is the protein signal after a long developing exposure time).

Figure 6A:
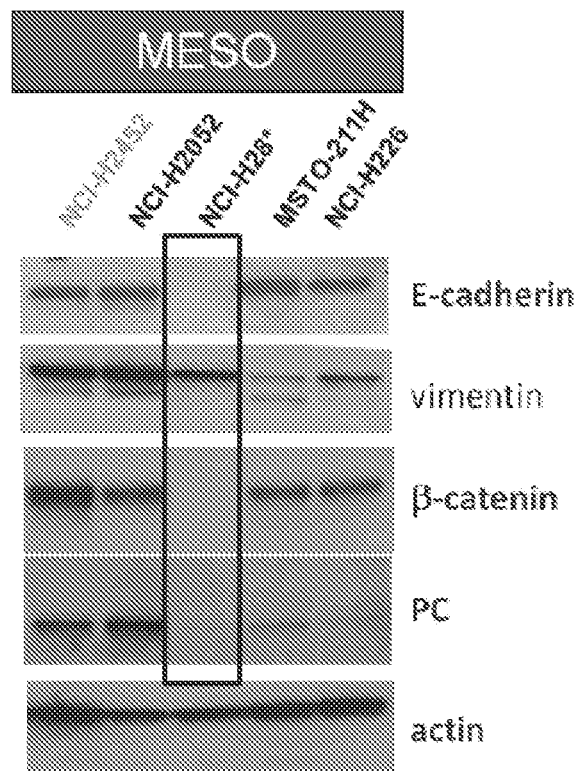
FIG. 6A depicts a western blot analysis of five mesothelioma cell lines for protein levels of E-cadherin, vimentin, PC (pyruvate decarboxylase), β-catenin; and actin (control).; in the presence (upper panel) and absence of (lower panel) of the GLS inhibitor BPTES.
Figure 6B:
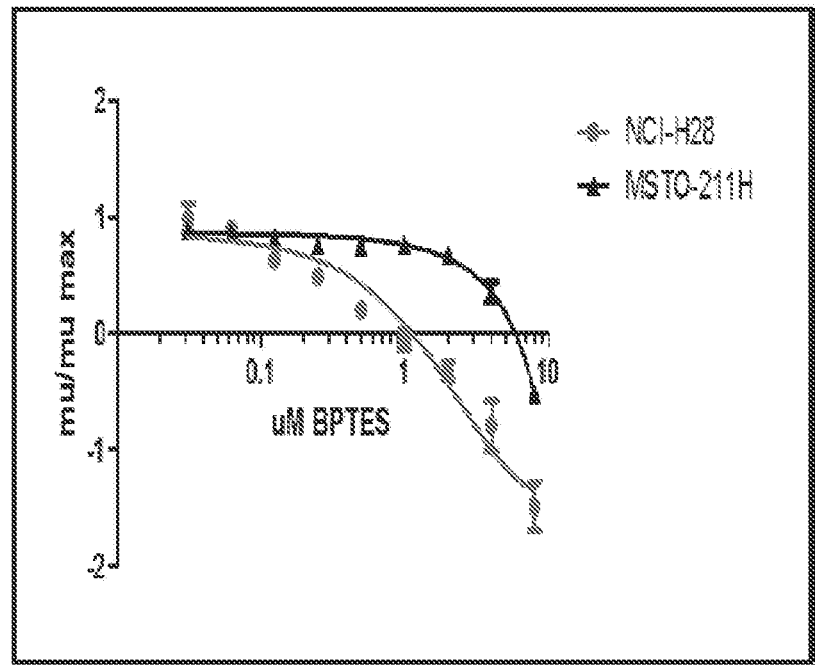
FIG. 6B depicts the growth response curves of two mesothelioma cell lines (H28; and MSTO-211H) treated with varying concentrations of the GLS inhibitor BPTES.

Western blot analysis (FIG. 6A) of the mesothelioma cancer cell lines indicated the most sensitive mesothelioma cancer cell line NCI-H28 (FIG. 6B), displayed low E-cadherin; high vimentin; and low pyruvate carboxylase protein levels were observed (FIG. 6A). Low E-cadherin/high vimentin are well-defined markers of cells that have a mesenchymal phenotype as characterized for example, in any one of the following references: (Yauch et al., (2005) Cin Cancer Res 11:24; Savagner et al., (2010) Ann Oncol. 21(suppl 7): vii89; Thiery et al., (2002) Nature Reviews Cancer June vol 2:442).

Example 3. Dependence of Select Cancer Cell Lines on GLS1 Activity

The effects of GLS1 inhibition on tumor cell growth using a published GLS1 inhibitor BPTES was analyzed (Steven J. McBryant et al. *Biochem Journal* 406, 407 (2007). The compound exhibits an $IC_{50}$ of ~80 nM using recombinant purified human GLS1 and GAC enzymes, acting as a non-competitive inhibitor of full-length enzyme (McBryant Supra; B. DeLaBarre et al. *Biochemistry* 50, 10764 (2011)). As published previously, BPTES is not an effective inhibitor of the GLS2 isoform of glutaminase ($IC_{50}$~90 μM). Furthermore, BPTES acts allosterically via a binding pocket located at the dimer-dimer interface of the GLS1 tetramer (A. Cassago et al., Mitochondrial localization and structure-based phosphate activation mechanism of Glutaminase C with implications for cancer metabolism. *Proc of the National Academy of Sciences* 109, 1092 (2012); McBryant Supra; DeLaBarre, Supra). A primary component of the binding pocket is a mobile loop (GLS1 residues 317-324) that becomes fixed upon BPTES binding. This loop differs in primary sequence between GLS1 and GLS2, thereby explaining the differential response of the two isoforms. BPTES was initially used to probe a small number of cancer cell lines of diverse origin in order to determine if there were any significant anti-proliferative effects of the compound in vitro. The lines investigated had been reported to exhibit sensitivity to GLS1 inhibition or knockdown (MDA-MB-231, SKBR3, HCT116, PC3, HepG2), one which was described as insensitive (Huh7) and two lines for which no published data was available at the time (A427, CAKI-1) (P. Gao et al. *Nature* 458, 762 (2009); J.-B. Wang et al. *Cancer Cell* 18, 207 (2010); F. Weinberg et al. *Proceedings of the National Academy of Sciences* 107, 8788 (2010); T. Cheng et al., *Proceedings of the National Academy of Sciences* 108, 8674 (2011)). As seen in FIG. 8A the expression of GLS1 is highly variable across this panel with levels highest in CAKI-1 renal carcinoma cells and lowest in the SKBR3 breast cancer cell line. Interestingly, the GAC splice variant appears to be the most highly expressed form of glutaminase in all of the cell lines that we have analyzed. After a 72 hr treatment of each cell line with BPTES, a wide range of sensitivities to the treatment was observed. Maximum response was seen in the A427 line and minimum effect seen in SKBR3 cells (FIG. 8B, FIG. 8C). MDA-MB-231, HepG2 and CAKI-1 cell lines exhibited modest sensitivity to BPTES treatment while SKBR3, HCT116, HUH7 and PC3 showed minimal response to the compound (FIG. 8C). Assessment of cell number by DNA content and direct cell counting demonstrated the same effect of BPTES treatment on cell proliferation as indicated by CellTiter-Glo at the 72 hr endpoint (FIGS. 9A and 9B).

Specificity of the GLS1 Inhibitor BPTES

Figure 10A:
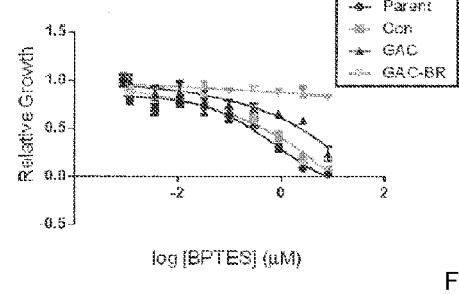
FIGS. 10A-10D show the anti-proliferative and metabolic effects of BPTES treatment are GLS1 dependent. A427 parent cells or lines stably expressing pLVX empty vector control (Con), wild-type GAC (GAC), or a BPTES-resistant GAC enzyme (GAC-BR) were treated with indicated concentrations of drugs in a 72 hr proliferation assay.
Figure 10B:
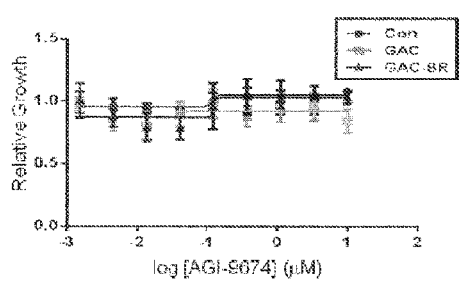
Figure 10C:
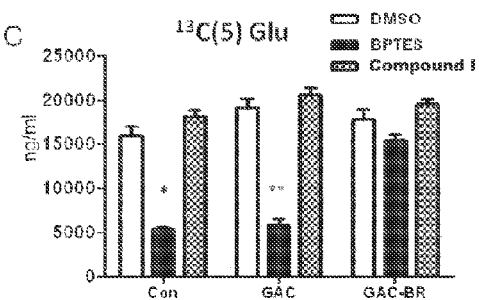
Figure 10D:
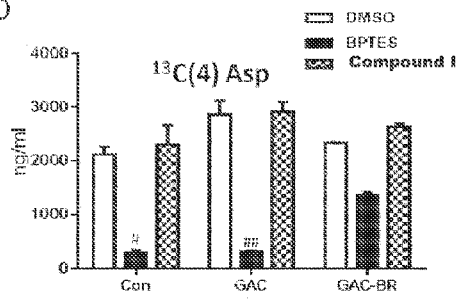
Figure 11A:
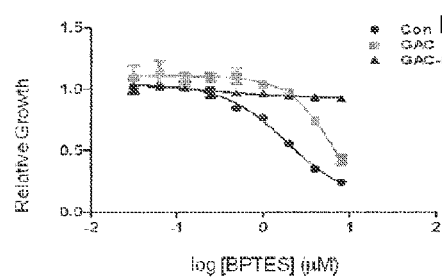
FIGS. 11A-11D show the anti-proliferative and metabolic effects of BPTES treatment are GLS1 dependent. MDA-MB-231 cell lines stably expressing empty vector control (Con), wild-type GAC (GAC), or a BPTES-resistant GAC enzyme (GAC-BR) were treated with indicated concentrations of drugs in a 72 hr proliferation assay.
Figure 11C:
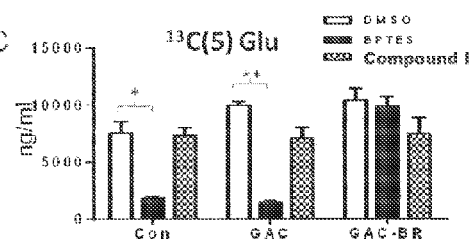
Figure 11B:
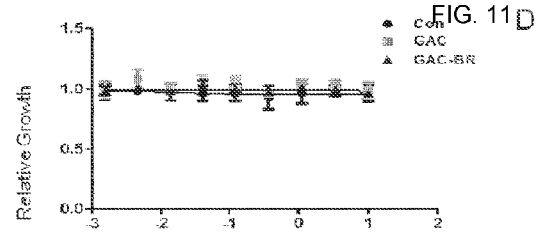
Figure 11D:
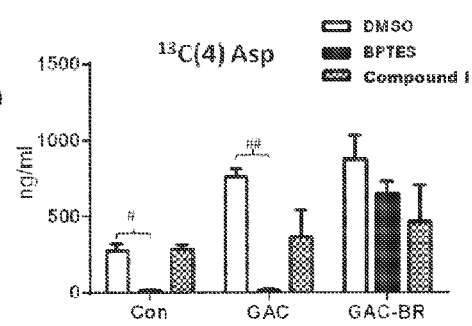
Figure 12:
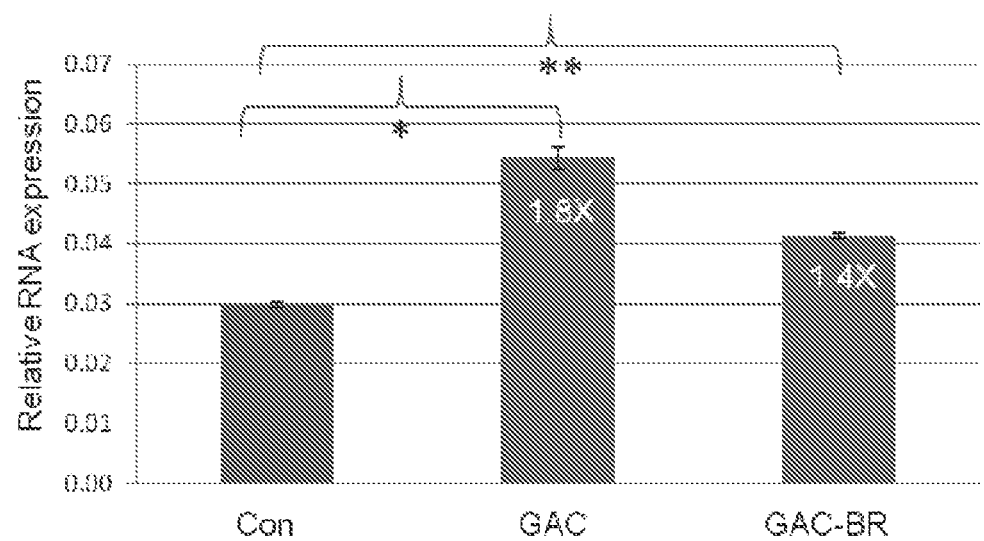
FIG. 12 shows the validation of expression levels of glutaminase C (GAC) in A427 pLVX-GAC and pLVX-GAC-BR cell lines. RNA expression analysis of pLVX-empty (Con), pLVX-GAC (GAC) and pLVX-GAC-BR (GAC-BR) cell lines using a glutaminase C splice variant (GAC-specific) Taqman probe. Relative expression normalized to actin is plotted with standard deviation. Fold increase in expression of GAC and GAC-BR lines is indicated (1.8× and 1.4×, respectively). Student t-test p-values were (*) p=0.003 and (**) p=0.001.

BPTES has been used frequently in the literature to elucidate biological functions of glutaminase (C. Yang et al. *Cancer Research* 69, 7986 (2009); M. J. Seltzer et al. *Cancer Research* 70, 8981 (2010); W. Liu et al., *Proc Natl Acad Sci USA* 109, 8983 (Jun. 5, 2012); P. A. Gameiro et al. *Cell Metab* 17, 372 (Mar. 5, 2013)). To confirm that the effects of BPTES on cells are specifically dependent on inhibition of GLS1 activity experiments were conducted to identify on- and off-target effects of this compound. A double point mutant of the GLS1 splice variant GAC, named GAC-BR (F318A and F322A) that is resistant to BPTES inhibition while maintaining its catalytic activity has been previously described B. DeLaBarre et al. *Biochemistry* 50, 10764 (2011)). BPTES-sensitive A427 and MDA-MB-231 cells were rendered resistant by stable overexpression of the GAC-BR mutant whereas cells expressing empty vector or GAC-WT retained significant sensitivity to BPTES (FIGS. 10A-10D, FIGS. 11A-11D). Levels of overexpression of the GAC WT and GAC-BR mutant were approximately 1.5-2.0 fold above endogenous GLS1 levels (FIG. 12). A biochemically inactive BPTES analogue, Compound I (FIG. 7) was used to treat the same cell lines and had no anti-proliferative effect on any of the cell lines (FIG. 10B, FIG. 11B). These data indicate that the anti-proliferative activity of BPTES is due to inhibition of GLS1 and not due to off-target effects.

Figure 13:
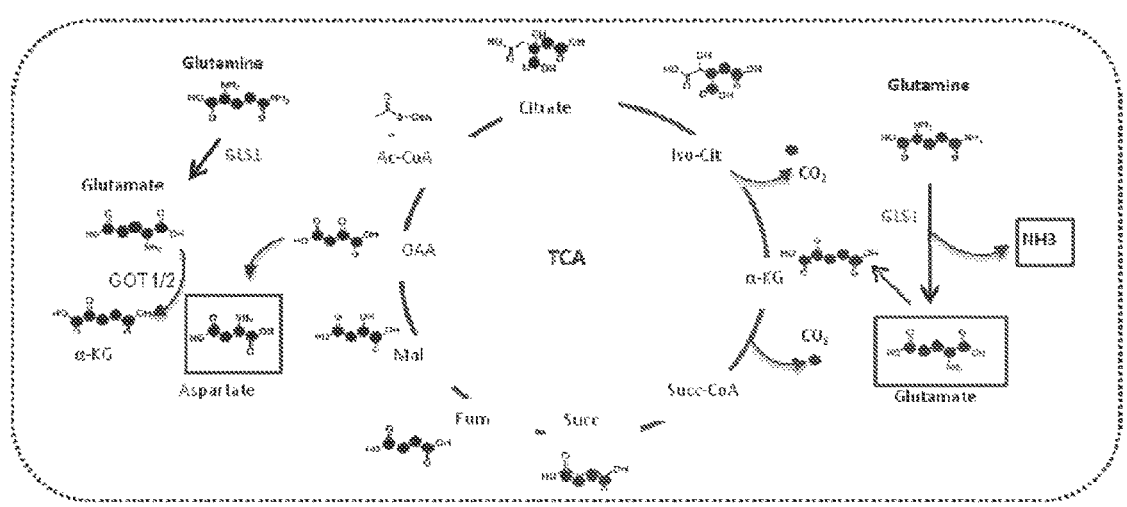
FIG. 13 depicts a diagram highlighting contribution of glutamine and GLS1 activity to the generation of glutamate, aspartate and TCA intermediates. The five carbons of glutamine highlighted in red represent the fully labeled $^{13}C$ isotopomer $^{13}C(5)$-glutamine. These $^{13}C$ atoms can be tracked through the immediate downstream product of glutaminase activity to $^{13}C(5)$-glutamate (boxed, right) and after multiple enzymatic steps to $^{13}C(4)$-aspartate (boxed, left).
Figure 14A:
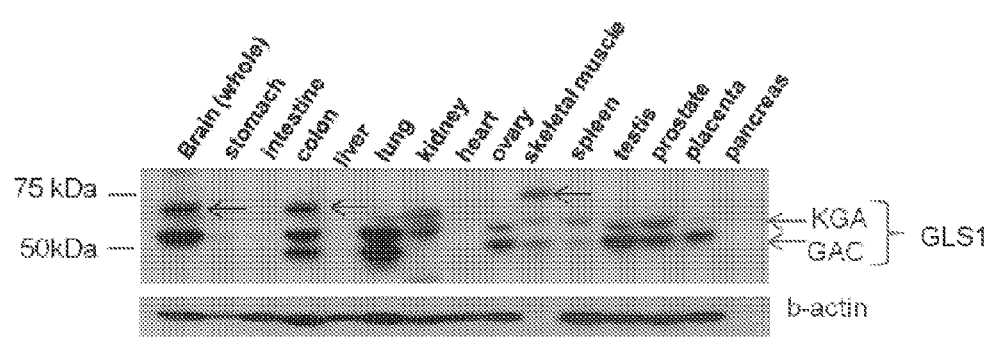
FIGS. 14A-B depict the expression of GLS1 (KGA and GAC) and GLS2 protein in normal human tissues.
Figure 14B:
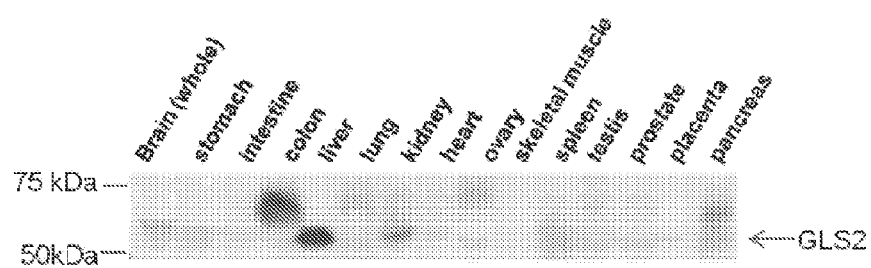

Several groups have shown that GLS inhibition leads to a decrease in cellular tricarboxylic acid cycle (TCA) intermediates downstream of GLS activity (P. Gao et al. *Nature* 458, 762 (2009); T. Cheng et al. *Proceedings of the National Academy of Sciences* 108, 8674 (2011)). Measurement of glutamate (the product of the glutaminase reaction) and aspartate (which derives both carbon and nitrogen from glutamate) are particularly sensitive readouts of glutaminase activity (FIG. 13). $^{13}$C labeled carbon in cells pre-treated with drug was tracked for 1 hr, followed by a 2 hr $^{13}$C(5)-Gln labeling period, via LC/MS. In MDA-MB-231 and A427 cells, GLS inhibition resulted in decreased label accumulation in glutamate and aspartate and these effects were rescued by the introduction of the GAC-BR mutant (FIGS. 10C and 10D and FIGS. 11C and 10D). Inactive Compound I had no effects on glutamate and aspartate labeling in these two lines (FIGS. 10C and 10D and FIGS. 11C and 10D). These data indicate that the effects of BPTES treatment on de novo synthesis of glutamate and aspartate from glutamine are due to specific inhibition of GLS1. The apparent on-target effects of BPTES in the A427 cell line also suggest that although there is detectable expression of GLS2 in this line, GLS1 inhibition alone is sufficient to cause significant anti-proliferative effects and impair glutamine metabolism.

In order to obtain more insight into the metabolic changes that might be relevant for sensitivity to GLS1 inhibition a diverse panel of 15 cell lines that included representatives from NSCLC (NCI-H1703, A427, LXF289, NCI-H838, NCI-H460, NCI-H1563), renal cell carcinoma (786-0, SLR20, SLR21, SLR24, RCC4) and breast carcinoma (MDA-MB-231, HS578T, HCC1395, SKBR3) were examined. Proliferation assays were coupled with a targeted intracellular metabolite analysis in each of the cell lines. While clear changes in cell numbers were observed in multiple cell lines with 72 hr of drug treatment, little or no effect of drug on cell numbers was observed after 24 hr (FIGS. 9A and 9B). As a result, assays were conducted to determine changes in metabolites after 24 hours of drug treatment to measure changes in cellular metabolism that occurred prior to a block in cell proliferation. Table 3 indicates the metabolite changes that correlated with the anti-proliferative effects of BPTES.

TABLE 3

Metabolite changes correlated with anti-proliferative effects of BPTES

| Metabolite | Pearson Correlation | P-value | Adjusted P-value |
|---|---|---|---|
| Adenosine triphosphate | 0.79 | 0.0002 | 0.03 |
| Adenosine diphosphate | 0.77 | 0.0004 | 0.03 |
| Uridine triphosphate | 0.75 | 0.0009 | 0.05 |
| L-Glutamic acid | 0.71 | 0.0020 | 0.05 |
| Phosphoenolpyruvic acid | 0.71 | 0.0023 | 0.05 |
| NADPH | 0.70 | 0.0024 | 0.05 |
| Citric acid | 0.70 | 0.0028 | 0.05 |
| Glutathione | 0.69 | 0.0030 | 0.05 |
| 3-Phosphoglyceric acid | 0.69 | 0.0034 | 0.05 |
| Oxidized glutathione | 0.68 | 0.0035 | 0.05 |
| NAD | 0.68 | 0.0036 | 0.05 |
| NADP | 0.67 | 0.0046 | 0.06 |
| Glucose 6-phosphate | 0.66 | 0.0056 | 0.07 |
| Phosphoserine | 0.62 | 0.0101 | 0.11 |
| L-Aspartic acid | 0.62 | 0.0105 | 0.11 |
| Fumaric acid | 0.78 | 0.0138 | 0.13 |
| L-Malic acid | 0.60 | 0.0139 | 0.13 |
| L-Glutamine | −0.58 | 0.0178 | 0.15 |
| D-2-Hydroxyglutaric acid | 0.38 | 0.1411 | 1 |
| D-Glyceraldehyde 3-phosphate | −0.38 | 0.1432 | 1 |
| L-Lactic acid | 0.38 | 0.1463 | 1 |
| Dihydroxyacetone phosphate | −0.38 | 0.1490 | 1 |
| Fructose 1,6-bisphosphate | −0.36 | 0.1675 | 1 |
| Oxoglutaric acid | 0.38 | 0.1825 | 1 |
| D-Ribose 5-phosphate | −0.33 | 0.2095 | 1 |
| D-Ribulose 5-phosphate | −0.29 | 0.2717 | 1 |
| L-Proline | 0.26 | 0.3254 | 1 |
| D-Glucose | 0.26 | 0.3317 | 1 |
| Pyruvic acid | 0.27 | 0.3767 | 1 |
| Succinic acid | 0.23 | 0.3814 | 1 |
| NADH | 0.44 | 0.3825 | 1 |
| Argininosuccinic acid | 0.24 | 0.3947 | 1 |
| Fructose 6-phosphate | 0.23 | 0.4015 | 1 |
| Acetyl-CoA | 0.32 | 0.4427 | 1 |
| Adenosine monophosphate | 0.19 | 0.4895 | 1 |
| Glucose 1-phosphate | 0.09 | 0.7787 | 1 |
| D-Sedoheptulose 7-phosphate | 0.02 | 0.9366 | 1 |

Figure 15:
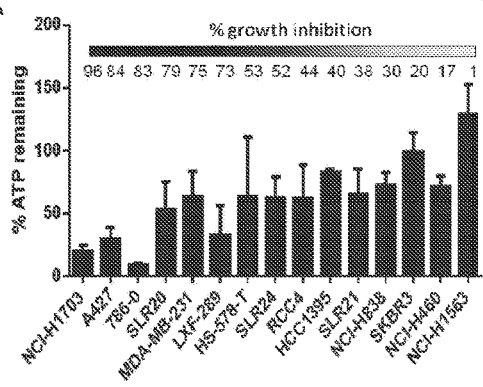
FIGS. 15A-15B depict the correlation between decreases in intracellular metabolite levels and anti-proliferative effects of GLS1 inhibition.
Figure 15:
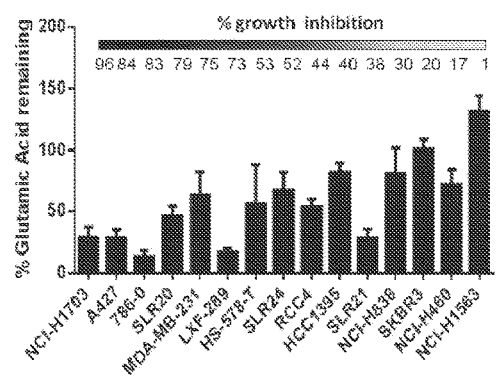

Notably, decreases in intracellular glutamate and ATP levels both correlate well with the anti-proliferative effects of GLS1 inhibition across this panel of cell lines (Pearson correlation of 0.71, p=0.002 and 0.79, p=0.0002, respectively). Glutamate can act as both an anaplerotic source for the TCA and as a precursor for the generation of glutathione (P. S. Ward, C. B. Thompson, *Cancer Cell* 21, 297 (Mar. 20, 2012)). Cells using glutamine and GLS1 as their primary source of intracellular glutamate were most sensitive to inhibition of GLS1. Decreases in cellular ATP correlated with anti-proliferative effects of the drug, consistent with glutamine supporting ATP production via the TCA and oxidative phosphorylation (P. Gao et al. *Nature* 458, 762 (2009)). While these correlations hold generally true across these cell lines, a clear sensitive population is not obvious from this limited panel of cells (FIGS. 15A and 15B).

What is claimed:

1. A method of treating a patient having cancer, the method comprising:
    acquiring an evaluation of or evaluating a patient sample, wherein the sample is evaluated for i) a level of E-cadherin expression or ii) a level of vimentin expression; and
    if the level of E-cadherin expression is low, or the level of vimentin expression is high, as compared to a reference standard, then
    administering to the patient in need thereof a therapeutically effective amount of an inhibitor of a glutamine-utilizing enzyme or a glutamine-depleting agent.

2. The method of claim 1, wherein the level of E-cadherin expression is evaluated by the level of E-cadherin protein expression.

3. The method of claim 1, wherein the level of vimentin expression is evaluated by the level of vimentin protein expression.

4. The method of claim 1, wherein the patient is administered a therapeutically effective amount of an inhibitor of a glutamine-utilizing enzyme.

5. The method of claim 4, wherein the inhibitor of a glutamine-utilizing enzyme inhibits a glutaminase.

6. The method of claim 5, wherein the inhibitor is bis-2-(5-phenylacetamido-1,2,4-thiadiazol-2-yl)ethyl sulfide (BPTES).

7. The method of claim 1, wherein the patient is administered a therapeutically effective amount of a glutamine depleting agent.

8. The method of claim 1, wherein the cancer is lung cancer.

9. The method of claim 8, wherein the lung cancer is non-small cell lung cancer.

10. A method of evaluating a patient having cancer for treatment with an inhibitor of glutamine-utilizing enzyme or a glutamine-depleting agent, the method comprising:
    evaluating a patient sample, wherein the sample is evaluated for i) a level of E-cadherin expression or ii) a level of vimentin expression; and
    if the level of E-cadherin expression is low, or the level of vimentin expression is high, as compared to a reference standard, then
    determining to treat the patient with the inhibitor of glutamine-utilizing enzyme or the glutamine-depleting agent.

11. The method of claim 10, wherein the sample is evaluated for i) a level of E-cadherin expression and ii) a level of vimentin expression.

12. The method of claim 10, wherein the sample is evaluated for low or decreased pyruvate carboxylase expression compared to a reference standard.

13. The method of claim 10, wherein the level of E-cadherin expression is evaluated by the level of E-cadherin protein expression.

14. The method of claim 10, wherein the level of vimentin expression is evaluated by the level of vimentin protein expression.

15. The method of claim 10, wherein the patient is evaluated for treatment with an inhibitor of a glutamine-utilizing enzyme.

16. The method of claim 15, wherein the inhibitor of a glutamine-utilizing enzyme inhibits a glutaminase.

17. The method of claim 16, wherein the inhibitor is bis-2-(5-phenylacetamido-1,2,4-thiadiazol-2-yl)ethyl sulfide (BPTES).

18. The method of claim 10, wherein the patient is evaluated for treatment with a glutamine depleting agent.

19. The method of claim 10, wherein the cancer is lung cancer.

20. The method of claim 19, wherein the lung cancer is non-small cell lung cancer.

* * * * *

UNITED STATES PATENT AND TRADEMARK OFFICE
CERTIFICATE OF CORRECTION

PATENT NO.         : 10,101,331 B2
APPLICATION NO.    : 15/444807
DATED              : October 16, 2018
INVENTOR(S)        : Jonathan Hurov et al.

Page 1 of 1

It is certified that error appears in the above-identified patent and that said Letters Patent is hereby corrected as shown below:

On the Title Page

(63) Related U.S. Application Data: delete "PCT/US2013/599967" and replace with -- PCT/US2013/059967 --.

Signed and Sealed this
Twenty-seventh Day of November, 2018

Andrei Iancu
*Director of the United States Patent and Trademark Office*